US012737887B1

(12) United States Patent
Singh et al.

(10) Patent No.: US 12,737,887 B1
(45) Date of Patent: Sep. 15, 2026

(54) APPARATUS FOR AND METHOD OF REAL-TIME GLOBAL POSITIONING OF IMAGES

(71) Applicant: Pramana, Inc., Cambridge, MA (US)

(72) Inventors: Tushar Singh, Bangalore (IN); Raghubansh Bahadur Gupta, Bangalore (IN); Prasanth Perugupalli, Cary, NC (US)

(73) Assignee: Pramana, Inc., Cambridge, MA (US)

( * ) Notice: Subject to any disclaimer, the term of this patent is extended or adjusted under 35 U.S.C. 154(b) by 0 days.

(21) Appl. No.: 19/388,398

(22) Filed: Nov. 13, 2025

(51) Int. Cl.
*G06T 7/00* (2017.01)
*G06T 3/4038* (2024.01)
(Continued)

(52) U.S. Cl.
CPC .......... *G06T 7/0012* (2013.01); *G06T 3/4038* (2013.01); *G06T 5/50* (2013.01); (Continued)

(58) Field of Classification Search
CPC ......... G06T 3/4038; G06T 2207/10056; G06T 2207/30024; G06T 11/00; G06T 2200/32; G06T 2207/20221; G06T 2207/10004; G06T 3/14; G06T 7/74; G06T 1/0007; G06T 3/047; G06T 7/194; G06T 5/50; H04N 23/698; H04N 2201/0079; H04N 1/3876; G06V 20/693; G06V 20/695; G06V 20/69; G06V 2201/03; G16H 30/20; G16H 30/40
See application file for complete search history.

(56) References Cited

U.S. PATENT DOCUMENTS 9,253,449 B2 * 2/2016 Steckhan .............. G06T 3/4038
2009/0262180 A1 * 10/2009 Kim ...................... G06T 3/4038 348/E5.042

(Continued)

FOREIGN PATENT DOCUMENTS

JP 2001512252 A 8/2001
WO 2021240545 A1 12/2021

OTHER PUBLICATIONS

Krishna et al, "GloFlow: Global Image Alignment for Creation of WholeSlide Images for Pathology from Video", "arXiv.orgOct. 28, 2020".

*Primary Examiner* — Courtney Joan Nelson
(74) *Attorney, Agent, or Firm* — CALDWELL LLC

(57) ABSTRACT

An apparatus and method for real-time global positioning of images. The apparatus includes at least a processor and a memory communicatively connected to the at least a processor. The memory instructs the processor to acquire, using an image acquisition engine, sequential image fields of view comprising a plurality of slide images, determine relative displacements between overlapping fields of view of the sequential image fields of view, and construct a system of linear equations representing the relative displacements. The processor is configured to stitch, using a positioning model, the sequential image fields of view by estimating the system of linear equations in matrix form as a function of weighted least-squares minimization, assigning global coordinates to each field of view in real-time, and generating a global mosaic as a function of the global coordinates.

20 Claims, 7 Drawing Sheets

(51) Int. Cl.
*G06T 5/50* (2006.01)
*G06T 7/194* (2017.01)
*G16H 30/20* (2018.01)
*G16H 30/40* (2018.01)

(52) U.S. Cl.
CPC ............. *G06T 7/194* (2017.01); *G16H 30/20* (2018.01); *G16H 30/40* (2018.01); *G06T 2207/10056* (2013.01); *G06T 2207/20221* (2013.01); *G06T 2207/30024* (2013.01)

(56) References Cited

U.S. PATENT DOCUMENTS

2016/0321809 A1 11/2016 Chukka et al.
2017/0111581 A1 * 4/2017 Muenzenmayer ... H04N 13/117
2020/0043134 A1 2/2020 Martin et al.

* cited by examiner

APPARATUS FOR AND METHOD OF REAL-TIME GLOBAL POSITIONING OF IMAGES

FIELD OF THE INVENTION

The present invention generally relates to the field of digital pathology. In particular, the present invention is directed to an apparatus for and a method of real-time global positioning of images.

BACKGROUND

Conventional Whole Slide Imaging (WSI) systems capture sequential fields of view (FOVs) and perform global positioning only after acquisition using graph-based optimization. This post-acquisition dependency causes delays and prevents downstream processing until stitching is complete. As a result, stitching errors are detected after acquisition, leading to rework and reduced efficiency in high-throughput imaging environments such as pathology laboratories.

SUMMARY OF THE DISCLOSURE

In an aspect, an apparatus for real-time global positioning of images includes at least a processor and a memory communicatively connected to the at least a processor. The memory contains instructions configuring the processor to acquire, using an image acquisition engine, sequential image fields of view, wherein the sequential image fields of view comprise a plurality of slide images, determine relative displacements between overlapping fields of view of the sequential image fields of view, construct a system of linear equations representing the relative displacements, and stitch, using a positioning model, the sequential image fields of view by estimating the system of linear equations in matrix form as a function of weighted least-squares minimization, assigning global coordinates to each field of view in real-time, and generating a global mosaic as a function of the global coordinates.

In another aspect, a method for real-time global positioning of images includes acquiring, using at least a processor and an image acquisition engine operating on the at least a processor, sequential image fields of view, wherein the sequential image fields of view comprise a plurality of slide images, determining, using at least a processor, relative displacements between overlapping fields of view of the sequential image fields of view, constructing, using the at least a processor, a system of linear equations representing the relative displacements, and stitching, using a positioning model, the sequential image fields of view by estimating the system of linear equations in matrix form as a function of weighted least-squares minimization, assigning global coordinates to each fields of view in real-time, and generating a global mosaic as a function of the global coordinates.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatus and methods for real-time global positioning of images. The apparatus includes at least a computing device comprised of a processor and a memory communicatively connected to the processor. The memory instructs the processor to acquire, using an image acquisition engine, sequential image fields of view, wherein the sequential image fields of view comprise a plurality of slide images. The processor determines relative displacements between overlapping fields of view of the sequential image fields of view. The processor constructs a system of linear equations representing the relative displacements. Additionally, the processor stitches, using a positioning model, the sequential image fields of view by estimating the system of linear equations in matrix form as a function of weighted least-squares minimization, assigning global coordinates to each field of view in real-time, and generating a global mosaic as a function of the global coordinates.

Figure 1:
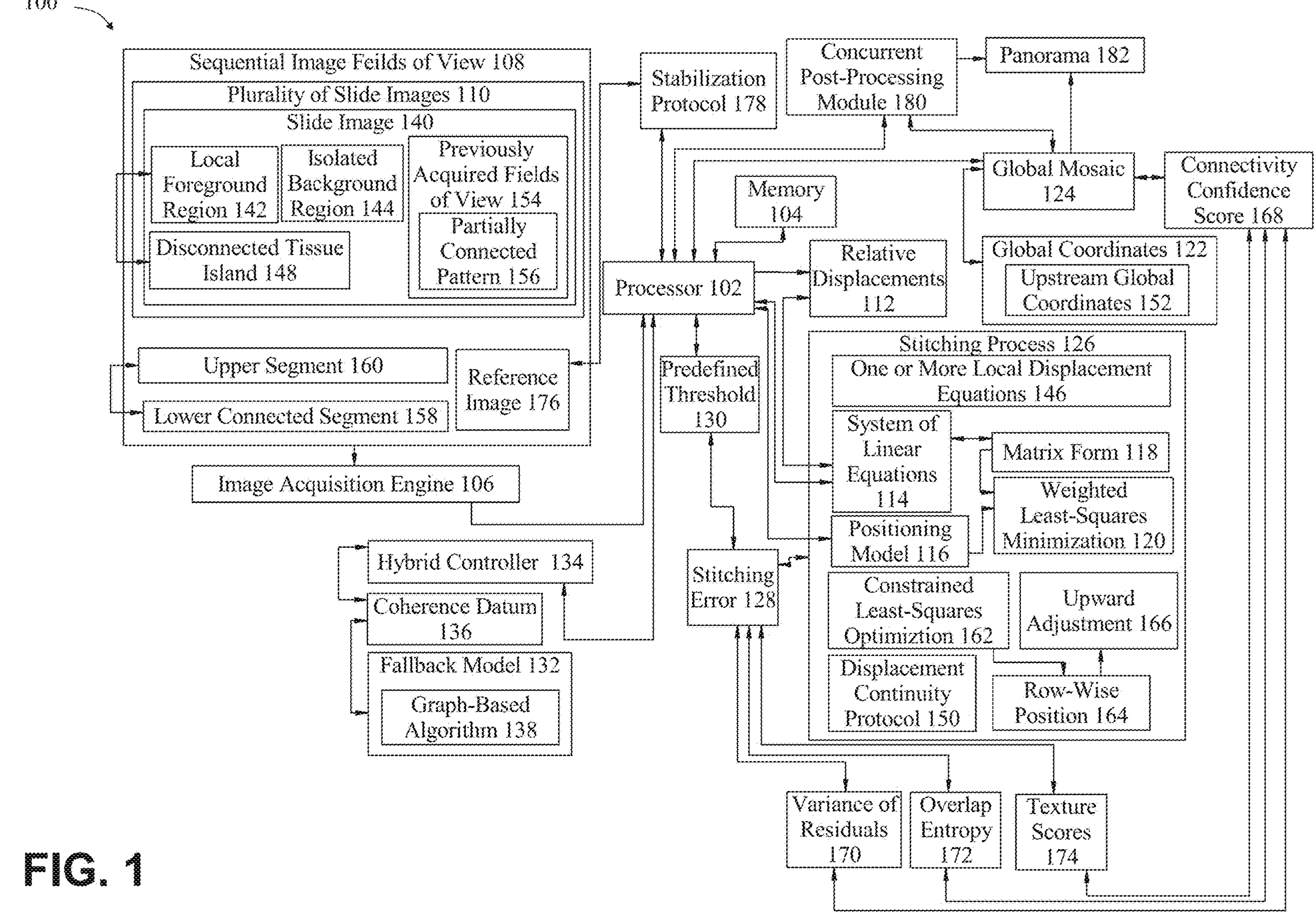
FIG. 1 is a block diagram of an apparatus for real-time global positioning of images.

Referring now to FIG. 1, the apparatus 100 includes a digital pathology and whole slide imaging (WSI) system configured to perform inline image positioning, real-time stitching, and concurrent post-processing during slide acquisition. The apparatus may address challenges associated with conventional WSI systems, which often rely on post-acquisition alignment, resulting in delays and limited feedback during imaging. By contrast, apparatus 100 may continuously compute and refine global coordinates of each field of view (FOV) as the slide is being scanned, allowing seamless, real-time generation of a stitched and processed digital slide. Apparatus 100 may include an image acquisition engine that captures sequential FOVs and streams them directly to a processing pipeline. An inline global positioning module may determine the relative displacements between overlapping image regions and assign corresponding global coordinates to each FOV during acquisition. An optimization engine may refine these coordinates using mathematical estimation and weighting techniques that reduce stitching errors and maintain geometric accuracy across the image grid. Certain FOVs may be designated as anchor points to stabilize global positioning, ensuring that all subsequent fields align to a consistent reference framework. The apparatus may also include a stitching error monitor that continuously evaluates displacement residuals to detect alignment inconsistencies. When alignment deviations exceed a predefined tolerance, the processor may invoke a fallback model such as a graph-based optimization method, recalibrating coordinates to restore positional accuracy. A concurrent post-processing module may operate in parallel with acquisition, performing blending, tiling, illumination correction, and panorama generation in real time as global coordinates become available. This module may utilize multi-threaded or GPU-accelerated computation to maintain synchronization with acquisition and reduce total processing time. The apparatus may further include a hybrid controller configured to apply linear or graph-based correction strategies based on spatial continuity, displacement variance, or connectivity confidence, thereby optimizing performance under varying tissue configurations. Apparatus 100 may also support advanced handling of complex tissue structures, including disconnected tissue islands, biopsy fragments, and partially connected regions. A displacement continuity protocol may be employed to maintain smooth spatial transitions, while local displacement equations may be adaptively weighted by connectivity confidence scores derived from image quality and overlap features. This design ensures that geometrically consistent regions exert greater influence on alignment and that stitching remains accurate even when tissue continuity is interrupted. Once alignment is complete, the concurrent post-processing module may generate a panoramic mosaic representing the entire specimen. The panoramic output may be displayed through a user interface, enabling interactive navigation, real-time monitoring, and quality assurance during or after acquisition. The interface may further allow visualization of stitching accuracy, alignment status, and image enhancement progress without interrupting ongoing operations. Through this configuration, apparatus 100 may operate as a fully integrated real-time imaging and reconstruction system that performs acquisition, positioning, optimization, correction, and post-processing simultaneously. This architecture may reduce overall WSI generation time, enhance spatial accuracy, increase imaging throughput, and provide immediate feedback during slide scanning, as described herein.

With continued reference to FIG. 1, an exemplary embodiment of apparatus 100 for real-time global positioning of images is illustrated. Apparatus 100 may include a processor 102 communicatively connected to a memory 104. As used in this disclosure, "communicatively connected" means connected by way of a connection, attachment, or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals there between may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, memory 104 may include a primary memory and a secondary memory. "Primary memory" also known as "random access memory" (RAM) for the purposes of this disclosure is a short-term storage device in which information is processed. In one or more embodiments, during use of the computing device, instructions and/or information may be transmitted to primary memory wherein information may be processed. In one or more embodiments, information may only be populated within primary memory while a particular software is running. In one or more embodiments, information within primary memory is wiped and/or removed after the computing device has been turned off and/or use of a software has been terminated. In one or more embodiments, primary memory may be referred to as "Volatile memory" wherein the volatile memory only holds information while data is being used and/or processed. In one or more embodiments, volatile memory may lose information after a loss of power. "Secondary memory" also known as "storage," "hard disk drive" and the like for the purposes of this disclosure is a long-term storage device in which an operating system and other information is stored. In one or remote embodiments, information may be retrieved from secondary memory and transmitted to primary memory during use. In one or more embodiments, secondary memory may be referred to as non-volatile memory wherein information is preserved even during a loss of power. In one or more embodiments, data within secondary memory cannot be accessed by processor. In one or more embodiments, data is transferred from secondary to primary memory wherein processor 102 may access the information from primary memory.

Still referring to FIG. 1, apparatus 100 may include a database. The database may include a remote database. The database may be implemented, without limitation, as a relational database, a key-value retrieval database such as a NOSQL database, or any other format or structure for use as database that a person skilled in the art would recognize as suitable upon review of the entirety of this disclosure. The database may alternatively or additionally be implemented using a distributed data storage protocol and/or data structure, such as a distributed hash table or the like. The database may include a plurality of data entries and/or records as described above. Data entries in database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in database may store, retrieve, organize, and/or reflect data and/or records.

With continued reference to FIG. 1, apparatus 100 may include and/or be communicatively connected to a server, such as but not limited to, a remote server, a cloud server, a network server and the like. In one or more embodiments, the computing device may be configured to transmit one or more processes to be executed by server. In one or more embodiments, server may contain additional and/or increased processor power wherein one or more processes as described below may be performed by server. For example, and without limitation, one or more processes associated with machine learning may be performed by network server, wherein data is transmitted to server, processed and transmitted back to computing device. In one or more embodiments, server may be configured to perform one or more processes as described below to allow for increased computational power and/or decreased power usage by the apparatus computing device. In one or more embodiments, computing device may transmit processes to server wherein computing device may conserve power or energy.

Further referring to FIG. 1, apparatus 100 may include any "computing device" as described in this disclosure, including without limitation a microcontroller, microprocessor, digital signal processor (DSP) and/or system on a chip (SoC) as described in this disclosure. Apparatus 100 may include, be included in, and/or communicate with a mobile device such as a mobile telephone or smartphone. Apparatus 100 may include a single computing device operating independently, or may include two or more computing devices operating in concert, in parallel, sequentially or the like; two or more computing devices may be included together in a single computing device or in two or more computing devices. Apparatus 100 may interface or communicate with one or more additional devices as described below in further detail via a network interface device. Network interface device may be utilized for connecting processor 102 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 102 may include but is not limited to, for example, a computing device or cluster of computing devices in a first location and a second computing device or cluster of computing devices in a second location. Apparatus 100 may include one or more computing devices dedicated to data storage, security, distribution of traffic for load balancing, and the like. Apparatus 100 may distribute one or more computing tasks as described below across a plurality of computing devices of computing device, which may operate in parallel, in series, redundantly, or in any other manner used for distribution of tasks or memory between computing devices. Apparatus 100 may be implemented, as a non-limiting example, using a "shared nothing" architecture.

With continued reference to FIG. 1, processor 102 may be designed and/or configured to perform any method, method step, or sequence of method steps in any embodiment described in this disclosure, in any order and with any degree of repetition. For instance, processor 102 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 102 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, processor 102 is configured to acquire, using an image acquisition engine 106, sequential image fields of view 108, wherein the sequential image fields of view 108 comprises a plurality of slide images 110. As used in this disclosure, an "image acquisition engine" is a component configured to capture visual data from a target area and convert it into a digital image. In an embodiment, the image acquisition engine 106 may format the digital image for processing, analysis, and the like. The image acquisition engine 106 may include hardware and software elements such as sensors, optics, actuators, control algorithms, and the like, that cooperate to acquire image data from a specimen, object, or scene. In a non-limiting example, the image acquisition engine 106 may include a digital microscope camera that scans a biological slide and transmits image frames to a processing system. In another non-limiting example, an image acquisition engine 106 may include an industrial camera used in automated inspection to capture sequential images of items on a conveyor belt for defect detection. In a non-limiting example, the image acquisition engine 106 may include a digital pathology scanner that moves a microscope stage to different coordinates on a glass slide, captures high-resolution images of each region through an objective lens, and streams the data to a processing unit for stitching or analysis. In another non-limiting example, the image acquisition engine 106 may include a fluorescence imaging subsystem that sequentially illuminates a pathology slide with different excitation wavelengths and acquires multichannel images corresponding to specific biomarkers.

With continued reference to FIG. 1, as used in this disclosure, "sequential image fields of view" are a plurality of discrete image regions that are captured in a defined order. Without limitation, the sequential image fields of view 108 may be a plurality of discrete image regions that are captured in a defined order to form a continuous or tiled representation of a larger area. In an embodiment, each field of view may represent a specific localized region imaged by the acquisition system, and the sequence may define the spatial or temporal order in which these regions are captured. In a non-limiting example, sequential image fields of view 108 may include adjacent image tiles captured across a microscope slide to reconstruct a high-resolution composite image of a tissue sample. In a non-limiting example, sequential image fields of view 108 may include consecutive 512×512 pixel images captured along the X and Y axes of a pathology slide during whole-slide scanning, such that when assembled, the individual images form a seamless virtual slide. In another non-limiting example, sequential image fields of view 108 may correspond to tiled brightfield images of a stained tissue section, captured row by row as the imaging stage advances systematically under the objective lens.

With continued reference to FIG. 1, as used in this disclosure, a "slide image" is a digital image representing a defined region of a specimen mounted on a microscope slide. In an embodiment, the slide image 140 may be acquired using optical imaging techniques such as brightfield, fluorescence, phase contrast microscopy, and the like. Without limitation, the slide image 140 may reflect the morphology, staining, and/or fluorescence patterns of the specimen within the imaged field of view. In a non-limiting example, a slide image 140 may be a high-resolution brightfield image of a hematoxylin and eosin (H&E) stained tissue section obtained from a whole-slide imaging system. In another non-limiting example, a slide image 140 may be a fluorescence image of an immunohistochemically labeled tissue section showing biomarker expression within a specific region of interest on the pathology slide.

With continued reference to FIG. 1, in a non-limiting example, the processor 102 may be configured to control a motorized microscope stage and an automated optical imaging subsystem to acquire sequential image fields of view 108 from a pathology slide. The image acquisition engine 106 may move the stage in a raster or serpentine pattern beneath a fixed objective lens, pausing at predetermined coordinates to capture each image field of view. The optical subsystem may include a high-resolution digital camera or CMOS sensor that captures an image of each field, while the processor 102 coordinates stage movement, focus adjustment, and image capture timing. The sequential image fields of view 108 thus obtained may collectively form a digital mosaic of the entire slide or a selected region of interest. In another non-limiting example, the processor 102 may employ an autofocus mechanism, such as contrast-based or laser-based focus tracking, to ensure that each field of view is captured sharply despite variations in slide thickness or cover slip height. The image acquisition engine 106 may also include a scanning objective turret to switch between magnifications such as, 10×, 20×, or 40×, depending on the desired imaging resolution. Each captured image is transmitted to the processor 102, which may align, correct, and stitch the images together in real time to generate a continuous digital slide image 140. In a further non-limiting example, the acquisition process may use multispectral or fluorescence imaging technology. The image acquisition engine 106 may sequentially illuminate the specimen with different excitation wavelengths, capturing multiple fields of view under each condition to detect the presence and distribution of specific fluorescent biomarkers. The processor 102 may then register the resulting images into multi-layer composite datasets that represent both spatial and spectral information. In another non-limiting example, line-scan or time-delay integration (TDI) imaging technology may be used to acquire sequential image fields of view 108 in a continuous scanning motion. Rather than capturing discrete images at fixed positions, the image acquisition engine 106 may move the slide continuously beneath a linear array detector, producing seamless strips of image data that the processor 102 subsequently segments into fields of view or assembles into a full-resolution slide image 140.

Still referring to FIG. 1, processor 102 is configured to determine relative displacements 112 between overlapping fields of view of the sequential image fields of view 108. As used in this disclosure, "relative displacement" is the positional difference between two or more image fields of view. Without limitation, the two or more image fields of view may represent adjacent or overlapping regions of a specimen. Relative displacement may quantify how much one field of view is shifted, translated, rotated, and the like, with respect to another in one or more spatial dimensions, such as the X, Y, or Z axes. Determining relative displacement may allow the apparatus 100 to align or register sequential image fields of view 108 accurately so that they can be combined into a coherent, continuous slide image 140. In a non-limiting example, relative displacement may be calculated by comparing common image features, such as cellular patterns or staining landmarks, appearing in overlapping regions of adjacent fields of view. The processor 102 may compute pixel-level shifts by performing correlation or feature-matching operations, such as phase correlation, normalized cross-correlation, or key point-based registration using algorithms like SIFT or SURF. As used in this disclosure, a "correlation matching operation" is a computational process in which corresponding regions of two or more images are compared based on the similarity of their pixel intensity patterns. The correlation matching operation may evaluate how well one image region aligns with another by computing a correlation metric, such as cross-correlation or normalized cross-correlation, that quantifies the degree of similarity between overlapping pixel values. The position that yields the highest correlation value may indicate the best alignment or match between the compared image regions, thereby identifying the relative displacement between them. In a non-limiting example, a correlation matching operation may be used to align two overlapping brightfield pathology images by scanning one image over another pixel by pixel and computing the correlation coefficient at each position until the point of maximum correspondence is found. In another non-limiting example, the processor 102 may employ phase correlation in the frequency domain to determine subpixel alignment between consecutive fields of view captured from a pathology slide. As used in this disclosure, a "feature-matching operation" is a computational process in which distinct and identifiable image features are detected, extracted, and compared between two or more images to determine spatial correspondence. Without limitation, image features may include edges, corners, blobs, texture patterns, and the like. Unlike correlation-based methods that rely on raw pixel intensity comparisons, feature-matching operations may identify keypoints or descriptors that represent the structural content of an image and then match those descriptors across images to infer geometric transformations such as translation, rotation, or scaling. In a non-limiting example, a feature-matching operation may involve detecting nuclei boundaries or glandular structures in adjacent pathology image fields of view, extracting local descriptors using algorithms such as Scale-Invariant Feature Transform (SIFT), Speeded-Up Robust Features (SURF), or Oriented FAST and Rotated BRIEF (ORB), and matching these descriptors to calculate the relative displacement between images. In another non-limiting example, a feature-matching operation may be used to align fluorescence images captured under different staining channels by comparing common structural features of the tissue visible across those channels.

With continued reference to FIG. 1, as used in this disclosure, an "overlapping field of view" is an imaged region that shares a common portion of the specimen area with an adjacent field of view. Overlap between fields of view may be intentionally introduced during image acquisition to ensure continuity and accurate alignment when reconstructing a larger composite image from sequential captures. The degree of overlap may be defined as a percentage of the total image area, for example, 5-15%, and serves to provide sufficient shared content for computational registration. In a non-limiting example, overlapping fields of view may occur when a motorized microscope stage moves the slide in small increments such that each new image frame contains a portion of the previous frame. This shared region may enable the image processing system to determine the spatial relationship between consecutive images and correct for small mechanical inaccuracies, optical distortions, or motion errors.

With continued reference to FIG. 1, in a non-limiting example, processor 102 may determine relative displacements 112 between overlapping fields of view of the sequential image fields of view 108 by implementing one or more image registration and alignment technologies that operate on digital pathology data. The processor 102 may receive sequential image fields of view 108 acquired by the image acquisition engine 106, each containing a partially overlapping region with its neighboring image. Using computational imaging techniques, the processor 102 may analyze these overlapping portions to identify corresponding spatial features and compute the relative offsets required for precise alignment. Without limitation, this process may be performed through a combination of correlation matching operations, feature-matching operations, and the like, allowing accurate determination of translational, rotational, or even non-linear displacements between adjacent images. In a non-limiting example, the processor 102 may employ phase correlation algorithms to calculate subpixel-level displacements by transforming the overlapping image regions into the frequency domain and analyzing phase shifts. As used in this disclosure, "phase correlation algorithms" are computational techniques used to determine the translational displacement between two or more overlapping images by analyzing their frequency-domain representations. The fundamental principle of a phase correlation algorithm is that a shift in the spatial domain may correspond to a linear phase difference in the frequency domain. Without limitation, by computing the cross-power spectrum of two images and analyzing the phase information, the algorithm may identify the relative displacement as the location of a distinct peak in the correlation surface, which indicates the amount and direction of the shift required to align the images. In a non-limiting example, a phase correlation algorithm may be applied to two overlapping brightfield image fields of view captured from adjacent regions of a pathology slide. The processor 102 may transform both images into the frequency domain using a Fast Fourier Transform (FFT), compute the normalized cross-power spectrum by dividing the product of one image's Fourier transform and the complex conjugate of the other by its magnitude, and then apply an inverse Fourier transform to obtain a correlation surface. The location of the maximum peak within this surface may indicate the pixel offset between the two image fields of view. In another non-limiting example, phase correlation algorithms may be enhanced to achieve subpixel accuracy by interpolating the correlation peak or fitting it with a mathematical function such as a paraboloid. Such precision may be critical in digital pathology applications, where even micron-level misalignments between adjacent slide images 110 can introduce stitching artifacts or analytical inaccuracies. In another non-limiting example, phase correlation algorithms may be robustly applied even when intensity variations occur due to uneven illumination, staining variability, or imaging noise, because the method relies primarily on phase information rather than raw pixel intensity values. Without limitation, this characteristic may make phase correlation well-suited for high-throughput slide scanners and other imaging systems where precise registration of sequential image fields of view 108 is required for accurate digital reconstruction of pathology specimens. As used in this disclosure, "subpixel-level displacements" are relative positional shifts between two or more images that are smaller than the size of a single pixel in the digital image grid. Subpixel-level displacements may represent fractional pixel movements along one or more spatial dimensions, typically the X and Y axes, and correspond to fine-scale variations in image alignment or specimen positioning that occur during image acquisition. Determining subpixel-level displacements may allow for extremely precise image registration, enabling adjacent or overlapping image fields of view to be aligned with accuracy beyond the resolution of the sensor's pixel grid. In a non-limiting example, subpixel-level displacements may be identified by applying interpolation or phase-based computational methods that estimate fractional offsets between image regions. For instance, a phase correlation algorithm may determine the relative shift between two overlapping pathology image tiles by locating the peak in the correlation surface and then fitting that peak with a continuous mathematical function, such as a Gaussian or paraboloid, to estimate its position with subpixel precision. In another non-limiting example, a feature-based alignment algorithm may calculate subpixel-level displacements by analyzing corresponding landmarks, such as nuclei boundaries or tissue structures, across overlapping image regions and using bilinear or spline interpolation to refine the spatial transformation. Accurate detection of subpixel-level displacements may be especially valuable in digital pathology and other high-resolution imaging systems, where even micron-scale misalignments can lead to stitching seams, morphological distortions, or analytical errors. Without limitation, by compensating for these fractional offsets, the imaging system may produce a seamless composite slide image 140 with consistent geometric accuracy and reliable feature continuity across the entire specimen.

Additionally, and/or alternatively, the processor 102 may utilize normalized cross-correlation methods to determine the position that yields the highest similarity score between corresponding image intensities. As used in this disclosure, a "normalized cross-correlation method" is a computational image analysis technique used to measure the similarity between two or more image regions while accounting for variations in illumination, contrast, or intensity scaling. The method may operate by sliding one image (or a portion of it) over another and calculating a correlation coefficient at each position that quantifies how well their pixel intensity patterns match. Unlike standard cross-correlation, the normalized cross-correlation method divides the correlation value by the product of the standard deviations of the compared regions, thereby normalizing the result and ensuring that the correlation value is independent of absolute brightness or contrast differences. In a non-limiting example, the normalized cross-correlation method may be used to determine the relative displacement between overlapping fields of view captured from adjacent regions of a pathology slide. The processor 102 may select an overlapping region from one image tile and compute normalized cross-correlation values as that region is shifted across its neighboring tile. The position where the correlation coefficient reaches its maximum value may indicate the best alignment between the two image regions, thereby defining the translational offset needed for registration. In another non-limiting example, normalized cross-correlation may be implemented in digital pathology systems to align brightfield or fluorescence images where staining intensity or illumination may vary between image captures. Without limitation, by normalizing the correlation computation, the method allows the processor 102 to identify accurate spatial correspondence between images despite differences in mean intensity or contrast caused by slide preparation or optical nonuniformity. In another non-limiting examples, the normalized cross-correlation method may be combined with subpixel interpolation techniques to refine displacement estimates, enabling subpixel-level alignment of adjacent image fields. This approach may be particularly useful in whole-slide imaging applications, where accurate registration of thousands of sequential image tiles is required to generate a continuous, high-resolution digital representation of the pathology specimen. In another non-limiting example, the processor 102 may perform feature-based registration by identifying and matching distinctive structures such as nuclei boundaries, glandular patterns, or other morphological features across the overlapping fields of view. These features may be detected using algorithms such as Scale-Invariant Feature Transform (SIFT), Oriented FAST and Rotated BRIEF (ORB), or Speeded-Up Robust Features (SURF). In an embodiment, the processor 102 may leverage machine learning or deep learning models trained to detect corresponding landmarks across image tiles with variable staining intensity, focus, or illumination. The processor 102 may use convolutional neural networks (CNNs) or transformer-based vision architectures to predict relative displacement vectors directly from the overlapping image data. Additionally, the processor 102 may apply image stitching and blending technologies, such as multi-band blending or gradient-domain fusion, to integrate the aligned image fields seamlessly and correct for edge artifacts. In an embodiment, hardware acceleration may be used to support this computation. The processor 102 may include or interface with graphics processing units (GPUs) or tensor processing units (TPUs) to perform high-speed parallel computations of displacement fields across large pathology slide datasets. The processor 102 may further employ autofocus and position feedback data from the image acquisition engine 106, such as encoder readings from the motorized stage or optical focus tracking signals, to refine the estimated displacements and ensure spatial consistency.

Still referring to FIG. 1, processor 102 is configured to construct a system of linear equations 114 representing the relative displacements 112. As used in this disclosure, a "system of linear equations" is a mathematical representation comprising two or more linear equations that relate multiple variables through linear relationships. Each equation in the system may express a constraint or relationship among the variables using coefficients and constants, and the collective set of equations can be solved simultaneously to determine the values of the unknown variables that satisfy all relationships at once. In an embodiment, the variables may represent positional parameters, such as the X and Y coordinates or displacement offsets, while the equations may define the relationships between these variables based on measured relative displacements 112 between overlapping image fields of view. Without limitation, the processor 102 may determine pairwise displacements between neighboring FOVs, where each displacement represents an "edge" connecting two adjacent image tiles. These displacements may then be formulated as linear equations in a two-dimensional coordinate space. For each pair of overlapping fields, the processor 102 may express the relationship as:

$$a_i x + b_i y = d_i$$

where x and y represent the global positional coordinates to be solved, $a_i$ and $b_i$ are coefficients defining the spatial orientation or weighting of the displacement constraint, and $d_i$ is the measured displacement, for example, the offset determined by a correlation or feature-matching operation. In a non-limiting example, the processor 102 may generate one such equation for each measured displacement between adjacent FOVs, thereby forming a connected network of linear constraints that describe the relative spatial arrangement of all captured image tiles. The resulting system of equations may then be assembled in matrix form 118 and solved using computational linear algebra techniques such as least-squares minimization or matrix decomposition to determine the best-fit global positions for all fields of view. The matrix form 118 may be expressed as:

$$A_x = b$$

where A represents the coefficient matrix containing the coefficients ($a_i$, $b_i$, and related terms) that define the spatial relationships and orientations between overlapping image fields of view, x represents the vector of unknown global positional coordinates corresponding to the image tiles (for example, the X and Y positions of each field of view within the reconstructed slide), and b represents the vector of measured displacements obtained from the image alignment process (for example, the translation offsets determined through correlation or feature-matching operations). In another non-limiting example, the processor 102 may assign weighting factors to certain equations to account for differences in measurement confidence, for instance, giving greater weight to displacement measurements derived from high-contrast image regions and lower weight to those from low-texture or noisy regions. In a further non-limiting example, the processor 102 may extend the formulation to include correction terms that compensate for stage nonlinearity, optical distortion, or mechanical drift, allowing the system to produce a globally optimized alignment across the entire slide. Without limitation, the construction of a system of linear equations 114 representing the relative displacements 112 allows processor 102 to translate localized pairwise measurements between overlapping image fields of view into a unified global coordinate framework. This linear algebraic approach ensures that the sequentially captured pathology images are geometrically consistent, spatially accurate, and ready for seamless reconstruction into a complete digital slide.

Still referring to FIG. 1, processor 102 is configured to stitch, using a positioning model 116, the sequential image fields of view 108 by estimating the system of linear equations 114 in matrix form 118 as a function of weighted least-squares minimization 120, assigning global coordinates 122 to each field of view in real-time, and generating a global mosaic 124 as a function of the global coordinates 122. As used in this disclosure, a "positioning model" is a computational framework that identifies how individual image fields of view (FOVs) are spatially arranged, aligned, and transformed within a global coordinate system. The positioning model 116 may describe the geometric relationships among sequentially acquired FOVs, incorporating parameters such as translation, rotation, or scale to accurately reconstruct the specimen's spatial layout. The positioning model 116 may further account for systematic errors such as stage drift, lens distortion, or focus variation to achieve precise image registration. In a non-limiting example, the positioning model 116 may describe the relative motion of a microscope stage during whole-slide imaging, mapping each image tile's local coordinates to its position on the overall slide. In another non-limiting example, the positioning model 116 may represent the coordinate transformations used to align fluorescence and brightfield images of the same tissue region captured under different imaging modalities.

With continued reference to FIG. 1, as used in this disclosure, a "matrix form" is a mathematical expression that represents a system of equations using a matrix-based notation. Without limitation, the matrix for may express in which coefficients, variables, and constants are organized into structured arrays. Representing equations in matrix form 118 may allow the processor 102 to efficiently perform linear algebraic operations, such as inversion, decomposition, or optimization, to solve for unknown parameters. In a non-limiting example, the processor 102 may represent the spatial displacement equations between overlapping FOVs in matrix form 118 as A x=b, where A is a coefficient matrix defining pairwise constraints, x is a vector of unknown positional coordinates, and b is a vector of measured displacements. In another non-limiting example, matrix form 118 may be used to represent transformations applied to align image tiles through affine or homography matrices, enabling scalable computation of slide-level alignment. As used in this disclosure, a "weighted least-squares minimization" is an optimization technique in which a processor determines the best-fit solution to a system of equations by minimizing the sum of squared residuals between observed and estimated values, while assigning different weights to individual equations or data points based on their relative reliability. Without limitation, this may allow more accurate or higher-confidence displacement measurements to influence the alignment more strongly than uncertain ones. In a non-limiting example, the processor 102 may assign higher weights to displacement measurements obtained from high-contrast tissue regions and lower weights to measurements from low-texture or noisy areas, thereby improving overall spatial accuracy. In another non-limiting example, the processor 102 may use weighted least-squares minimization 120 to refine the global alignment of FOVs when stitching together hundreds of pathology image tiles that vary in illumination or focus quality. As used in this disclosure, "global coordinates" are the spatial positions of individual image fields of view expressed within a unified coordinate framework that represents their placement across the entire imaged specimen. Assigning global coordinates 122 may ensure that each FOV's position is consistent relative to all others, enabling precise reconstruction of the whole specimen in a common spatial reference. In a non-limiting example, the processor 102 may assign global X-Y coordinates to each image tile of a scanned pathology slide, determining each tile's absolute position within the overall slide mosaic. In another non-limiting example, global coordinates 122 may be used to align multi-plane Z-stack images, where each plane's position is defined relative to a shared three-dimensional reference frame. As used in this disclosure, "real-time" is the capability of a system or processor to perform computations or operations concurrently with data acquisition or with negligible delay relative to the imaging process. Real-time processing may allow immediate updating, correction, or visualization of results as new data are acquired. In a non-limiting example, the processor 102 may calculate relative displacements 112 and assign global coordinates 122 to each newly captured FOV while the slide is still being scanned, thereby generating a continuously updating digital mosaic. In another non-limiting example, a real-time feedback loop may enable the microscope stage to correct its movement trajectory dynamically based on alignment data computed on-the-fly. As used in this disclosure, a "negligible delay" is a time interval between sequential computational or imaging operations that is sufficiently short so as not to interrupt or slow the overall process of data acquisition or processing. The negligible delay may be effectively insignificant relative to the imaging or scanning cycle time, such that operations appear continuous or real-time. The duration that constitutes a negligible delay may include time intervals on the order of microseconds to a few milliseconds, for example, less than about 1-10 milliseconds, depending on the operational parameters of the system. In a non-limiting example, a negligible delay may occur when processor 102 computes and updates the global coordinates 122 of each newly captured image field of view within approximately 1 millisecond after the image acquisition engine 106 completes capture, thereby allowing seamless, real-time stitching during continuous slide scanning. In another non-limiting example, a negligible delay may include a processing latency of less than 5 milliseconds between capturing adjacent fields of view, ensuring that the imaging pipeline operates at full acquisition speed without perceptible pause or lag.

With continued reference to FIG. 1, as used in this disclosure, a "global mosaic" is a composite digital image formed by stitching together multiple sequential image fields of view 108 into a single, spatially continuous representation of an entire specimen or region of interest. The global mosaic 124 may integrate all aligned image tiles using their assigned global coordinates 122, creating a unified image that preserves the correct spatial relationships between features across the specimen. In a non-limiting example, the processor 102 may generate a global mosaic 124 of a pathology slide by combining thousands of 40× magnification image tiles into a seamless high-resolution image suitable for diagnostic review. In another non-limiting example, a global mosaic 124 may represent a multi-channel fluorescence composite image, where images captured under different excitation wavelengths are aligned and blended into a single, layered visualization of biomarker expression across the tissue sample.

With continued reference to FIG. 1, in a non-limiting example, processor 102 may be configured to perform a stitching process 126 in which the sequential image fields of view 108 acquired from a pathology slide are combined into a continuous, spatially accurate composite image. The stitching process 126 may begin with the processor 102 receiving the sequential image fields of view 108 from the image acquisition engine 106, each field of view partially overlapping with its neighboring field to provide common visual features. Using a positioning model 116, the processor 102 may determine the relative displacements 112 between overlapping image pairs and express these spatial relationships as a system of linear equations 114. The system of equations may then be represented in matrix form 118, where the coefficients define spatial constraints between adjacent fields, the variables correspond to the global coordinates 122 of the image tiles, and the constants represent the measured displacements derived from correlation or feature-matching operations. The processor 102 may solve the system of equations as a function of weighted least-squares minimization 120, allowing it to compute the most consistent global arrangement of all image fields of view while accounting for differences in measurement confidence or imaging quality. Higher weights may be assigned to displacement measurements obtained from regions with distinct tissue features, such as nuclei boundaries or sharp morphological landmarks, while lower weights may be applied to regions with low contrast or uneven staining. Through this optimization process, the processor 102 may minimize cumulative alignment errors and derive a globally consistent spatial configuration for the slide. Once the global solution is obtained, the processor 102 may assign global coordinates 122 to each image field of view in real-time, updating their positions dynamically as new fields are acquired. This allows continuous feedback and immediate placement of image tiles into their proper positions within the global coordinate system without interrupting slide scanning. The processor 102 may generate a global mosaic 124 by blending or fusing the aligned image tiles based on their assigned global coordinates 122. The blending process may include techniques such as intensity normalization, feathering, or gradient-domain fusion to smooth boundaries and eliminate visible seams between adjacent tiles. In a non-limiting example, the stitching process 126 may be used in a whole-slide imaging system to generate a seamless, high-resolution composite of an entire histopathology slide captured at 40× magnification. In another non-limiting example, the same process may be applied in a fluorescence imaging workflow, where multiple color channels are aligned and merged into a unified multi-layer mosaic that accurately represents biomarker distribution across the specimen. Through this integrated stitching process 126, processor 102 may reconstruct a geometrically accurate and diagnostically reliable digital slide in real-time.

With continued reference to FIG. 1, in a non-limiting example, processor 102 may be implemented within a whole-slide imaging system configured to digitize an entire hematoxylin and eosin (H&E) stained pathology slide at 40× magnification. The image acquisition engine 106 may capture thousands of sequential image fields of view 108 (FOVs), each approximately 512×512 pixels in size and acquired with about 10% overlap between neighboring images. As each FOV is acquired, the processor 102 may execute a correlation matching operation to determine the relative displacement between adjacent images by analyzing overlapping tissue features, for example, nuclei boundaries, stromal fibers, or glandular edges. These displacements may then be expressed as linear equations of the form ($a_i x + b_i y = d_i$), representing the spatial relationships between adjacent image tiles in two-dimensional space. The processor 102 may then assemble the full set of displacement equations into matrix form 118 (A x=b), where A represents the coefficient matrix defining the geometric relationships among all neighboring tiles, x represents the vector of unknown global coordinates 122 for each image field, and b represents the vector of measured displacements. The processor 102 may solve this matrix equation using weighted least-squares minimization 120, assigning higher weights to displacement measurements obtained from high-contrast tissue regions, for example, regions rich in nuclei or well-defined epithelial boundaries, and lower weights to measurements from low-contrast or artifact-prone regions, for example, blank slide regions or unevenly stained areas. Once the optimal solution is computed, the processor 102 may assign global coordinates 122 to each field of view in real-time, such that each newly captured image is immediately placed into its correct position within the global coordinate framework. The processor 102 may also perform intensity normalization to balance illumination variations and apply gradient-domain blending to remove visible seams at the boundaries of overlapping images. These steps may enable continuous and seamless reconstruction of the digital slide without interruption of image acquisition. In a specific non-limiting example, the processor 102 may stitch approximately 10,000 sequential FOVs covering a 15 mm×15 mm tissue section at 40× magnification. The stitching process 126 may complete in under 30 seconds, with a negligible delay, for example, less than about 5 milliseconds, between each image capture and coordinate assignment. The resulting output may be a high-resolution global mosaic 124, a seamless, spatially accurate digital composite image of the entire pathology slide suitable for diagnostic review, feature detection, and computational pathology analysis.

With continued reference to FIG. 1, processor 102 may be configured to monitor a stitching process 126, identify a stitching error 128 of the sequential image fields of view 108, wherein the stitching error 128 exceeds a predefined threshold 130, and compensate, using a fallback model 132, for the stitching error 128 of the stitching process 126. As used in this disclosure, a “stitching process” or “stitching” is a computational operation in which multiple sequential image fields of view 108 (FOVs) acquired from a specimen are spatially aligned, blended, and combined into a single continuous composite image. The single continuous composite image may also be referred to as a global mosaic 124. The stitching process 126 may determine the relative positions of overlapping FOVs, assigns global coordinates 122 to each, and merges the images so that structural and morphological features align seamlessly across tile boundaries. The stitching process 126 may include steps such as displacement estimation, coordinate calculation, intensity normalization, boundary blending, and the like. In a non-limiting example, the stitching process 126 may combine thousands of brightfield image tiles acquired at 40× magnification from a pathology slide into a unified digital slide representation suitable for diagnostic analysis. In another non-limiting example, the stitching process 126 may align and merge multiple fluorescence image channels representing distinct biomarkers into a single multi-layer composite. As used in this disclosure, a “stitching error” is the residual spatial misalignment or deviation between overlapping image fields of view after computational stitching has been performed. The stitching error 128 may quantify how accurately adjacent images are registered relative to their expected overlap, often expressed in terms of pixel offset, displacement magnitude, or alignment residual. A stitching error 128 may arise from stage drift, optical distortion, illumination variation, inaccuracies in displacement estimation, and the like. In a non-limiting example, a stitching error 128 may include a misalignment of more than about 2 pixels between adjacent image fields of view in a reconstructed pathology slide. In another non-limiting example, a stitching error 128 may include a geometric deviation greater than a predefined threshold 130, such as 1% of the field width, indicating the need for correction or recalibration. As used in this disclosure, a “predefined threshold” is a reference value established to determine acceptable performance, error tolerance, or quality control during image acquisition and stitching. The predefined threshold 130 may define the maximum allowable deviation or residual beyond which corrective actions are triggered automatically. The predefined threshold 130 may be determined empirically based on system calibration or application requirements. In a non-limiting example, a predefined threshold 130 may include a stitching error 128 limit of less than about 2 pixels or less than about 0.5 micrometers, beyond which the processor 102 initiates a fallback correction procedure. In another non-limiting example, the predefined threshold 130 may be dynamically adjusted based on magnification level, for example, 20× versus 40×, or image content complexity. As used in this disclosure, a "fallback model" is a computational framework activated when the primary stitching process 126 exceeds acceptable error limits or becomes unreliable. The fallback model 132 may serve as a corrective mechanism to restore spatial accuracy by performing a more comprehensive, often slower but more precise, global optimization of image alignment. In a non-limiting example, the fallback model 132 may include a graph-based global optimization algorithm that recalculates the spatial relationships between all image tiles in an offline mode, ensuring geometric consistency across the entire slide. In another non-limiting example, the fallback model 132 may reprocess only the affected region of interest (AOI) where stitching errors 128 exceed the predefined threshold 130, allowing targeted recalibration while preserving overall system throughput.

With continued reference to FIG. 1, in a non-limiting example, processor 102 may be configured to monitor the stitching process 126 by continuously calculating residual displacement errors between adjacent image tiles as they are aligned in real-time. If the processor 102 identifies a stitching error 128 that exceeds the predefined threshold 130, for example, a residual offset greater than 2 pixels or 1% of the tile width, the processor 102 may automatically trigger a fallback mechanism. As used in this disclosure, a "residual offset" is the remaining positional difference or misalignment between two overlapping image fields of view after an initial alignment or stitching operation has been performed. The residual offset may represent the portion of the displacement error that has not been fully corrected by the alignment algorithm and may be expressed in pixel units, micrometers, or as a percentage of the field of view size. The residual offset may serve as a quantitative measure of the stitching accuracy and may be used by the processor 102 to determine whether the alignment meets a predefined tolerance or requires additional correction. Without limitation, the fallback mechanism may initiate an offline graph-based global positioning algorithm, which may construct a complete network graph of all FOV relationships and perform a global optimization of tile positions to minimize cumulative alignment error across the entire slide. In a non-limiting example, the fallback model 132 may execute this graph-optimization procedure by recalculating the global coordinates 122 of each FOV based on all available pairwise displacement data, ensuring accurate alignment even in cases of stage drift, uneven illumination, or focus variation. As used in this disclosure, a "graph-optimization procedure" is a computational process in which spatial relationships among multiple image fields of view are represented and refined using a graph-based mathematical model, where each image tile is treated as a node and each measured displacement or overlap constraint between tiles is represented as an edge connecting those nodes. The graph-optimization procedure may seek to determine the globally consistent arrangement of all tiles by minimizing the cumulative error across all edges in the graph, often using optimization techniques such as least-squares minimization, gradient descent, or matrix-based solvers. This approach may allow the processor 102 to reconcile local alignment errors and produce an optimized global configuration that best satisfies all pairwise positional relationships simultaneously. Continuing, without limitation, the fallback correction may apply to the entire slide or to localized regions exhibiting significant stitching discrepancies. Once recalibrated, the corrected global coordinates 122 may be re-integrated into the real-time imaging workflow, maintaining system robustness without user intervention. Without limitation, this design may allow the invention to achieve both real-time stitching performance during normal operation and high-accuracy offline correction when discrepancies arise. By combining an inline stitching error 128 monitor with a fallback mechanism, processor 102 may reduce total processing time, enhance imaging throughput, and ensure diagnostic-level accuracy for digital pathology and related imaging workflows.

With continued reference to FIG. 1, processor 102 may be configured to instantiate a hybrid controller 134, wherein the hybrid controller 134 selects the fallback model 132 as a function of a coherence datum 136, wherein the fallback model 132 comprises a graph-based algorithm 138. As used in this disclosure, a "hybrid controller" is a control framework or computational module configured to dynamically select between multiple processing modes based on the operational state, data quality, or detected imaging conditions. Without limitation, the processing modules may include linear alignment correction, graph-based global optimization, and the like. The hybrid controller 134 may monitor performance parameters during the stitching process 126 and determines, in real-time or near real-time, whether to continue using an inline (real-time) correction model or to invoke a fallback (offline) correction model. The hybrid controller 134 may enable adaptive workflow flexibility by balancing speed and accuracy depending on the coherence and stability of the stitching data. In a non-limiting example, the hybrid controller 134 may operate inline to perform rapid, real-time linear displacement estimation under stable imaging conditions where alignment errors are within acceptable limits. However, when local inconsistencies are detected, such as significant stage drift, uneven illumination, or feature misregistration, the hybrid controller 134 may automatically transition to a graph-based offline optimization model to restore alignment accuracy. In another non-limiting example, the hybrid controller 134 may evaluate each region of the slide independently, applying linear correction to coherent areas with low variance and graph-based optimization to regions with higher displacement errors or inconsistent overlap features. As used in this disclosure, a "coherence datum" is a quantitative or qualitative indicator that represents the consistency, stability, or reliability of spatial relationships among sequential image fields of view 108. The coherence datum 136 may be computed from one or more parameters that reflect the quality of alignment or local image geometry. The coherence datum 136 may include, without limitation, spatial continuity, displacement variance, or a connectivity score. In a non-limiting example, spatial continuity may include a measure of how smoothly adjacent image fields align across a region of the slide, where high continuity indicates well-behaved motion and consistent displacement, and low continuity indicates irregular or distorted motion. In another non-limiting example, displacement variance may include the degree of variation in the measured displacements between neighboring fields of view, where a low variance implies stable stage movement and high variance suggests potential alignment drift or local deformation. In a further non-limiting example, a connectivity score may include a metric quantifying the number or strength of reliable overlap relationships between image tiles within a region, where higher scores may indicate robust interconnections suitable for linear alignment, and lower scores may trigger fallback to graph-based optimization.

With continued reference to FIG. 1, as used in this disclosure, a "graph-based algorithm" is a computational method that models the spatial relationships among image tiles as a connected graph and optimizes those relationships globally. In an embodiment, the graph-based algorithm 138 may achieve consistent alignment across all nodes or image tiles. In an embodiment, each image field of view may be represented as a node, and each measured overlap or displacement between neighboring images may represented as an edge that connects the corresponding nodes. The graph-based algorithm 138 may solve for the optimal positions of all nodes by minimizing cumulative alignment error across all edges, often using least-squares minimization, iterative solvers, or global optimization techniques. In a non-limiting example, the graph-based algorithm 138 may be employed as part of the fallback model 132 to perform global optimization of image positions across a pathology slide when inline stitching errors 128 exceed a predefined threshold 130. The graph-based algorithm 138 may process displacement data from thousands of overlapping image tiles, adjusting their global coordinates 122 to ensure that all local and global spatial relationships are coherent. In another non-limiting example, processor 102 may use the graph-based algorithm 138 to refine a large-scale digital slide at 40× magnification, where the method recalculates tile positions across multiple regions with inconsistent overlaps to achieve a globally optimized, distortion-free mosaic suitable for diagnostic imaging.

With continued reference to FIG. 1, processor 102 may be configured to segment a slide image 140 of the plurality of slide images 110 into a local foreground region 142 and an isolated background region 144, stitch, using one or more local displacement equations 146, each local region into the global mosaic 124, and compensate, using the fallback model 132, the stitching error 128 of the global mosaic 124. As used in this disclosure, a "slide image" is a digital image representing a defined region of a specimen mounted on a microscope slide. In an embodiment, the slide image 140 may be acquired using an imaging system such as a whole-slide scanner, a microscope-based imaging engine, and the like. The slide image 140 may correspond to a single field of view or an individual image tile that captures optical information, for example, color, intensity, or fluorescence, from the specimen at a specific magnification level. Without limitation, a plurality of slide images 110 collectively may represent the entire specimen when stitched together. In a non-limiting example, the slide image 140 may include a 2048×2048 pixel brightfield image of a stained tissue section captured at 40× magnification. In another non-limiting example, a slide image 140 may include a fluorescence image highlighting biomarker distribution within a specific tissue region. As used in this disclosure, a "local foreground region" is a segmented portion of a slide image 140 that contains meaningful specimen information. Without limitation, the local foreground region 142 may include tissue structures, cells, and/or other biologically relevant features. The local foreground region 142 may represent the portion of the image that contributes to the diagnostic or analytical content of the slide and serves as the primary input for image alignment and stitching. In a non-limiting example, a local foreground region 142 may include a densely stained epithelial tissue area that contains well-defined cellular morphology, nuclei, and extracellular matrix. In another non-limiting example, the local foreground region 142 may correspond to an area of fluorescence signal indicating biomarker expression in tumor cells. As used in this disclosure, an "isolated background region" is a portion of a slide image 140 that lacks meaningful specimen content and is generally composed of uniform background or empty areas, such as regions of the slide without tissue, mounting medium, or stain. The isolated background region 144 is typically excluded or de-emphasized during stitching and analysis to prevent alignment errors or computational noise. In a non-limiting example, an isolated background region 144 may include a blank area of the glass slide containing only mounting medium or air bubbles without tissue. In another non-limiting example, an isolated background region 144 may include an unstained or low-signal zone in a fluorescence image where no cellular structures are present. As used in this disclosure, a "local displacement equation" is a mathematical relationship that defines the relative spatial offset between adjacent image tiles or between local regions within neighboring slide images 110. The local displacement equation may quantify the positional shift required to align one region with another within the overlapping area and may be expressed as a linear or affine equation. In a non-limiting example, a local displacement equation may describe small variations in alignment across a tissue boundary region, allowing local correction prior to integration into the global mosaic 124. As used in this disclosure, a "local region" is a sub-area of a slide image 140 that is processed independently or semi-independently for alignment, stitching, or analysis. A local region may include either a foreground region containing tissue content or a background region containing minimal information, depending on the segmentation results. In a non-limiting example, a local region may represent a 512×512 pixel patch extracted from a larger slide image 140 for localized displacement analysis. In another non-limiting example, a local region may correspond to a user-defined area of interest (AOI) within a tissue section targeted for high-resolution re-stitching or re-alignment.

With continued reference to FIG. 1, in a non-limiting example, processor 102 may be configured to segment each slide image 140 of the plurality of slide images 110 into a local foreground region 142 and an isolated background region 144. The segmentation may be performed using intensity thresholding, edge detection, or deep-learning-based tissue detection to distinguish tissue-containing regions from non-tissue areas. The processor 102 may employ intensity thresholding, a pixel-based technique that separates tissue from the background based on brightness or color intensity values. In brightfield imaging, tissue regions may exhibit higher optical density due to staining, for example, hematoxylin and eosin coloration, whereas the background appears bright or near white. The processor 102 may therefore classify pixels below a certain intensity threshold as tissue and pixels above the threshold as background. For instance, regions with a mean pixel intensity below about 200, on a 0-255 grayscale scale, may be identified as potential foreground tissue regions. In another non-limiting example, the processor 102 may apply edge detection algorithms, such as Sobel, Canny, or Laplacian filters, to identify spatial gradients and delineate the boundaries of tissue structures. These edge features may be used to refine the segmentation mask generated by intensity thresholding, ensuring that fine morphological details such as nuclei contours, glandular outlines, or tissue boundaries are preserved. Without limitation, this step may be particularly valuable for differentiating tissue fragments that are closely spaced or partially overlapping within the same slide image 140. In another non-limiting example, the processor 102 may implement deep-learning-based tissue detection, such as a convolutional neural network (CNN) or U-Net segmentation model trained on annotated pathology images. This approach may allow the system to learn complex features that distinguish tissue from mounting medium, air bubbles, or slide artifacts. The deep-learning model may analyze spatial texture, color distribution, and morphological context to generate highly accurate tissue masks even under variable staining or illumination conditions. For example, the model may identify lightly stained connective tissue as part of the foreground while excluding faint optical noise or debris from the background. In an embodiment, the segmentation output may include a binary or probabilistic mask that clearly separates the local foreground regions 142, such as tissue-containing areas, from the isolated background regions 144, such as non-tissue areas. The processor 102 may then use these masks to guide the stitching process 126, applying local displacement equations 146 only within the segmented tissue regions and excluding background zones from the alignment computation. This selective approach may reduce computational overhead, prevent alignment errors introduced by empty slide areas, and improve the overall accuracy and stability of the global mosaic 124 reconstruction. Continuing, once the local regions are segmented, the processor 102 may perform stitching using one or more local displacement equations 146, aligning each local region within the global coordinate framework defined by the global mosaic 124. Each local displacement equation may define the positional correction needed to align the local foreground regions 142 of adjacent slide images 110 while excluding or minimizing the influence of isolated background regions 144. In a non-limiting example, the processor 102 may compute local displacements for each foreground region using correlation or feature-matching techniques applied only to high-content tissue areas, such as those containing dense nuclei or glandular boundaries. The resulting local displacement equations 146 may be solved to position each local region within the global mosaic 124, thereby ensuring high-precision alignment across the specimen. If the processor 102 detects a stitching error 128 within the global mosaic 124, such as local misalignment exceeding a predefined threshold 130, it may invoke the fallback model 132, which may include a graph-based optimization algorithm, to compensate for the error. The fallback correction may refine the global coordinates 122 of the affected regions or the entire mosaic to restore spatial coherence. In another non-limiting example, the process may enable accurate, content-aware stitching in digital pathology workflows. For instance, during reconstruction of a 40× magnification whole-slide scan, the processor 102 may ignore empty slide regions and instead prioritize alignment of tissue-dense foreground areas, reducing computational load while maintaining diagnostic accuracy. Without limitation, by integrating local displacement estimation, segmentation, and fallback correction, processor 102 may generate a seamless, high-fidelity global mosaic 124 with reduced error propagation and improved stitching reliability.

With continued reference to FIG. 1, wherein the local foreground region 142 may correspond to a disconnected tissue island 148. As used in this disclosure, a "disconnected tissue island" is an isolated region of biological tissue present on a microscope slide that is not physically contiguous with other tissue regions within the same specimen area. A disconnected tissue island 148 may occur naturally due to the specimen's morphology, or it may result from sample preparation artifacts such as sectioning breaks, folding, incomplete mounting, and the like. The disconnected tissue island 148 each may represent independent local foreground regions that must be individually identified, aligned, and positioned within the global mosaic 124 to maintain the spatial integrity of the reconstructed slide. In a non-limiting example, a disconnected tissue island 148 may include a fragmented piece of tumor tissue separated from the main biopsy section by a small gap of unstained glass, which may occur when the tissue section tears during microtomy. In another non-limiting example, a disconnected tissue island 148 may include a small lymphoid aggregate or satellite nodule located several millimeters away from the primary tissue section on the same slide. In a further non-limiting example, in immunofluorescence or multiplex imaging workflows, a disconnected tissue island 148 may correspond to a dispersed cluster of cells or organoid structures embedded within a gel matrix, appearing as separate, non-contiguous regions of fluorescence signal. With continued reference to FIG. 1, in a non-limiting example, processor 102 may be configured to recognize that a local foreground region 142 corresponds to a disconnected tissue island 148 and process it independently within the stitching and alignment pipeline. During segmentation, the processor 102 may identify each disconnected island by detecting spatial discontinuities between tissue clusters in the slide image 140, using techniques such as connected-component labeling, morphological filtering, or contour analysis. Once identified, each disconnected tissue island 148 may be assigned its own local coordinate reference and associated local displacement equations 146 that define how that specific region aligns relative to nearby image tiles or to the global coordinate system. Without limitation, because disconnected tissue islands 148 may be spatially isolated and lack direct overlap with other tissue regions, the processor 102 may employ a graph-based optimization or fallback model 132 to determine their relative placement within the global mosaic 124. In this context, each tissue island may be treated as an independent node within a larger spatial graph, connected to other nodes through estimated positional relationships or stage metadata. The processor 102 may use these relationships to compute the global coordinates 122 of each island, ensuring that all disconnected tissue regions are accurately positioned within the overall digital slide. In a non-limiting example, during a 40× magnification whole-slide scan, the processor 102 may identify three disconnected tissue islands 148, one large central tissue section and two smaller fragments separated by background. The hybrid controller 134 may position the large central region using linear-algebra-based displacement equations, while invoking the graph-based fallback algorithm to optimize the placement of the smaller islands relative to the central structure. This process may allow the system to preserve accurate global spatial relationships across all tissue fragments, ensuring that the reconstructed digital slide remains diagnostically coherent even when the specimen is physically fragmented or discontinuous.

With continued reference to FIG. 1, wherein the local foreground region 142 may correspond to biopsy fragments.

As used in this disclosure, "biopsy fragments" are discrete sections of biological tissue obtained during a biopsy procedure that are mounted together on a microscope slide but are physically separated by background areas. Without limitation, the background areas may include blank regions of glass, mounting medium, empty space, and the like. Each biopsy fragment may represent an individual portion of the sampled tissue and may differ in size, orientation, or thickness, often as a result of the sampling and sectioning process. Without limitation, because biopsy fragments are not contiguous, they may be individually segmented, aligned, and spatially registered within the imaging workflow to form a coherent digital representation of the entire specimen. In a non-limiting example, biopsy fragments may include multiple tissue cores from a core needle biopsy that have been placed on a single slide for histopathological evaluation, with each fragment separated by several millimeters of empty slide background. In another non-limiting example, biopsy fragments may include small mucosal samples from a gastrointestinal biopsy or needle aspirate fragments from a lymph node, each appearing as an isolated tissue region separated by clear mounting medium. In another non-limiting example, in multiplex immunofluorescence imaging, biopsy fragments may correspond to distinct tissue cores from a tissue microarray (TMA), where each fragment is independently stained and imaged as a separate region but ultimately reconstructed into a unified digital mosaic for analysis. In a non-limiting example, processor 102 may be configured to segment the local foregrounds within a slide image 140 such that each disconnected tissue island 148 or biopsy fragment is independently identified as a distinct local region. The segmentation process may employ intensity thresholding, edge detection, or deep-learning-based tissue detection to distinguish tissue from background, generating a binary or probabilistic mask that isolates each fragment. Once isolated, the processor 102 may position each local foreground region 142 using local displacement equations 146 derived from adjacent image fields of view, thereby ensuring accurate alignment within the local coordinate framework. Continuing, because the biopsy fragments are separated by background areas and therefore lack direct overlap between image tiles, the processor 102 may invoke a graph-based optimization algorithm, as part of the fallback model 132, to compute the global coordinates 122 for each fragment. Each biopsy fragment may be represented as a node within a graph, connected by edges defined by estimated stage coordinates, spatial proximity, or other positional metadata. The processor 102 may perform graph optimization to minimize overall positional error and generate a global mosaic 124 in which all disconnected tissue islands 148 and biopsy fragments are correctly placed relative to one another. In a non-limiting example, during a 40× magnification whole-slide scan of a core needle biopsy specimen containing five tissue fragments, the processor 102 may segment and align each fragment individually. Local displacement equations 146 may position the tiles covering each fragment, while the graph-based fallback model 132 may refine the global arrangement of all fragments across the slide, compensating for stage drift or coordinate offsets. Without limitation, this process may ensure that even when tissue is fragmented and spatially separated by background, the resulting global mosaic 124 remains geometrically accurate and diagnostically coherent, preserving the spatial context required for digital pathology analysis.

With continued reference to FIG. 1, processor 102 may be configured to adjust, using a displacement continuity protocol 150, upstream global coordinates 152 of previously acquired fields of view 154 of the sequential image fields of view 108, wherein the previously acquired fields of view 154 comprises a partially connected pattern 156. As used in this disclosure, a "displacement continuity protocol" is a computational procedure implemented by a processor to ensure that positional relationships among sequential image fields of view 108 (FOVs) remain spatially continuous and consistent over time as new images are acquired. The displacement continuity protocol 150 may establish a smooth and coherent transition between neighboring image tiles by monitoring, adjusting, and, if necessary, recalibrating the global positions of previously aligned FOVs based on updated displacement data. The displacement continuity protocol 150 may preserve the geometric integrity of the overall mosaic even when incremental misalignments or motion drift are detected during the scanning process. In a non-limiting example, the displacement continuity protocol 150 may continuously compute relative displacements 112 between the current FOV and its immediate neighbors, compare them with expected values from the existing positioning model 116, and adjust global coordinates 122 to maintain consistent spatial continuity. In another non-limiting example, the displacement continuity protocol 150 may apply weighted averaging or local smoothing functions to distribute small alignment corrections across multiple FOVs, thereby preventing cumulative stitching errors 128 as the imaging process progresses.

With continued reference to FIG. 1, as used in this disclosure, "upstream global coordinates" are the global positional values assigned to previously acquired image fields of view that have already been stitched into the growing global mosaic 124. The term "upstream" refers to their temporal acquisition order, meaning these coordinates were determined prior to the current FOV being captured, and their influence on the subsequent alignment of downstream images. The upstream global coordinates 152 may serve as reference points for maintaining continuity in the overall coordinate system. In a non-limiting example, the upstream global coordinates 152 may correspond to the X-Y positions of a sequence of image tiles acquired in earlier rows of a raster scan. In another non-limiting example, the upstream global coordinates 152 may be adjusted slightly to compensate for cumulative drift detected in later-acquired FOVs, ensuring consistent registration across the entire slide. As used in this disclosure, "previously acquired fields of view" are image tiles that were captured earlier in the sequential image acquisition process. In an embodiment, previously acquired fields of view 154 may already be incorporated into the partially completed global mosaic 124. Without limitation, the previously acquired FOVs 154 may serve as spatial anchors for the alignment of newly captured images. In a non-limiting example, previously acquired fields of view 154 may include the first several hundred tiles captured along the top region of a slide before the imaging stage advances to lower rows. In another non-limiting example, previously acquired FOVs 154 may refer to tissue areas scanned in prior sessions that are re-referenced for alignment when rescanning overlapping or adjacent regions. As used in this disclosure, a "partially connected pattern" is a spatial configuration in which some of the image fields of view overlap or share alignment constraints with neighboring fields. This pattern may arise when tissue coverage across the slide is non-uniform or when certain regions are missing due to gaps, blank background, or disconnected tissue fragments. In such cases, only subsets of the image fields form directly connected clusters, while others remain isolated or sparsely linked through limited overlap relationships. In a non-limiting example, a partially connected pattern 156 may occur when scanning a tissue sample with multiple separate fragments on a single slide, where only adjacent fragments have overlapping image regions. In another non-limiting example, a partially connected pattern 156 may occur in fluorescence imaging, where only regions containing labeled structures provide usable overlap information for alignment.

With continued reference to FIG. 1, in a non-limiting example, processor 102 may be configured to adjust, using a displacement continuity protocol 150, the upstream global coordinates 152 of previously acquired fields of view 154 when the system detects deviations in spatial alignment caused by stage drift, cumulative rounding error, local distortion, and the like. The displacement continuity protocol 150 may evaluate the measured displacements between the newly acquired FOV and its adjacent upstream neighbors and compute a correction function that propagates small positional adjustments backward through the sequence of already-stitched images. This may ensure that spatial continuity is maintained across the entire image mosaic. In a non-limiting example, the previously acquired FOVs 154 may form a partially connected pattern 156, such as when scanning multiple disconnected tissue islands 148 separated by large background gaps. The processor 102 may use the displacement continuity protocol 150 to update the upstream global coordinates 152 within the connected regions of the pattern, preserving relative geometry within each local cluster, while maintaining consistency with the broader global coordinate system. The processor 102 may then incorporate the updated displacements into the positioning model 116, ensuring that the new FOV aligns correctly with both its immediate neighbors and the previously scanned regions. In another non-limiting example, during a 40× magnification whole-slide scan, the processor 102 may detect a minor alignment drift between the 500th and 510th FOVs in a tissue fragment. Using the displacement continuity protocol 150, the apparatus 100 may automatically adjust the upstream global coordinates 152 of the preceding 500 tiles by subpixel increments, for example, less than about 1 pixel, maintaining a smooth transition between image fields. This adaptive correction enables the processor 102 to preserve spatial coherence across the entire partially connected pattern 156, resulting in a geometrically stable and high-fidelity global mosaic 124.

With continued reference to FIG. 1, processor 102 may be configured to identify a lower connected segment 158 that deviates from an upper segment 160 and adjust, using constrained least-squares optimization 162, a row-wise position 164, wherein adjusting the row-wise position 164 comprises an upward adjustment 166 of the lower connected segment 158. As used in this disclosure, a "lower connected segment" is a contiguous group of image fields of view (FOVs) located in a lower portion of a scanned slide or mosaic that are spatially connected to one another through overlapping or adjacent image relationships. The lower connected segment 158 may represent a region that forms part of the overall stitched image but may become misaligned relative to neighboring upper image regions due to cumulative stage drift, thermal expansion, alignment error during scanning, and the like. In a non-limiting example, a lower connected segment 158 may include several hundred image tiles acquired near the bottom of a whole-slide scan that collectively form a continuous tissue region. In another non-limiting example, a lower connected segment 158 may include a discrete tissue island positioned below the primary tissue section that deviates slightly from the expected coordinate position when integrated into the global mosaic 124. As used in this disclosure, an "upper segment" is a contiguous group of image fields of view located in an upper portion of the slide or mosaic that serves as a spatial reference for the alignment of subsequent segments. The upper segment 160 may include previously scanned image tiles that have already been aligned within the global coordinate framework and exhibit stable positional accuracy. In a non-limiting example, an upper segment 160 may consist of the first several rows of image tiles at the top of a slide scan that establish the baseline geometry for the remainder of the image acquisition process. In another non-limiting example, an upper segment 160 may include a well-aligned tissue fragment positioned above a lower region that requires correction. As used in this disclosure, a "constrained least-squares optimization" is a mathematical procedure used by a processor to compute the best-fit solution for positional adjustments while satisfying one or more predefined constraints. This optimization may minimize the sum of squared residual errors between measured and predicted positions but incorporates limiting conditions, such as fixed reference points, boundary limits, or allowable movement ranges, to preserve geometric consistency and prevent overcorrection. In a non-limiting example, constrained least-squares optimization 162 may be applied to determine the optimal adjustment of the lower connected segment's position relative to the upper segment 160, subject to the constraint that the upper region remains fixed. In another non-limiting example, the processor 102 may use this optimization to distribute correction values evenly across several rows of FOVs while maintaining continuity at segment boundaries. As used in this disclosure, a "row-wise position" is the spatial coordinate or alignment state of a sequence of image fields of view arranged along a single horizontal scanning path within the mosaic. The row-wise position 164 may define the vertical alignment relationship between consecutive rows of image tiles in the global coordinate system. In a non-limiting example, the processor 102 may determine the row-wise position 164 by calculating the mean vertical offset between adjacent rows based on overlap measurements. In another non-limiting example, the row-wise position 164 may include the cumulative vertical displacement for a given row relative to the initial top row, used to detect gradual drift over long scans. As used in this disclosure, an "upward adjustment" is a corrective modification applied to the vertical coordinates of one or more image fields of view to compensate for downward drift, mechanical shift, or accumulated alignment deviation in the imaging system. The upward adjustment 166 may effectively move the lower connected segment 158 in the positive vertical direction relative to the upper segment 160 to reestablish spatial continuity. In a non-limiting example, the upward adjustment 166 may involve translating all image tiles within the lower connected segment 158 by a small vertical offset, for example, less than about 5 micrometers or 1-2 pixels, determined through constrained least-squares optimization 162. In another non-limiting example, the processor 102 may apply a gradual upward correction across multiple rows to achieve smooth alignment with the upper segment 160 without introducing abrupt transitions.

With continued reference to FIG. 1, in a non-limiting example, processor 102 may be configured to identify a lower connected segment 158 that deviates from an upper segment 160 due to accumulated stage drift or mechanical variation during whole-slide imaging. The processor 102 may apply constrained least-squares optimization 162 to compute the optimal row-wise positional adjustment required to realign the lower connected segment 158 with the upper segment. The optimization may constrain the upper segment to remain fixed, treating it as the geometric reference, while minimizing the total squared displacement error between overlapping or adjacent FOVs across the segment boundary. The resulting correction may include an upward adjustment 166 of the lower connected segment 158, which repositions the affected image rows vertically to restore alignment continuity within the global mosaic 124. In a non-limiting example, during a 40× magnification whole-slide scan, if the processor 102 detects a gradual downward drift of approximately 3 micrometers across ten consecutive rows of image tiles, it may compute an upward adjustment 166 using constrained least-squares optimization 162 to bring the lower connected segment 158 back into registration with the upper segment. The adjustment may ensure smooth row-to-row alignment, eliminate visible stitching seams, and preserve the geometric fidelity of the reconstructed digital slide.

With continued reference to FIG. 1, processor 102 may be configured to generate a connectivity confidence score 168 as a function of variance of residuals 170, overlap entropy 172, and texture score 174 of the sequential image fields of view 108 and weight, using the connectivity confidence score 168, the one or more local displacement equations 146. As used in this disclosure, a "connectivity confidence score" is a quantitative measure that represents the reliability, stability, or trustworthiness of the spatial connection between neighboring image fields of view (FOVs) in a sequential imaging process. The connectivity confidence score 168 may provide a weighting factor that allows the processor 102 to evaluate how strongly two or more image tiles are spatially correlated, thereby influencing their contribution to the overall stitching or alignment model. A higher connectivity confidence score 168 may indicate a high degree of local consistency, for example, strong feature overlap, low residual error, and robust texture similarity, while a lower score reflects weak or uncertain alignment between adjacent regions. In a non-limiting example, the processor 102 may compute the connectivity confidence score 168 as a composite metric derived from multiple parameters, such as the variance of residuals 170, overlap entropy 172, and texture score 174, each representing a distinct aspect of spatial or visual reliability. The score may be used as a weighting factor in the local displacement equations 146, ensuring that highly reliable image connections exert greater influence on the global optimization process than uncertain or noisy ones. As used in this disclosure, the "variance of residuals" is a statistical measure representing the degree of variability or inconsistency in the residual displacement errors between overlapping regions of adjacent image fields of view. Low variance may indicate that the alignment between images is stable and consistent across the overlap, while high variance suggests irregularity or misalignment, potentially caused by uneven illumination, focus drift, tissue deformation, and the like. In a non-limiting example, the variance of residuals 170 may be computed as the variance of pixel-level displacement vectors or correlation error maps within the overlap region. In another non-limiting example, a variance of residuals 170 below about 0.5 pixels$^2$ may correspond to a strong and stable alignment suitable for high confidence weighting, while a variance above about 2 pixels$^2$ may indicate unreliable alignment. As used in this disclosure, "overlap entropy" is a measure of the information content or structural complexity within the overlapping region between adjacent image tiles. Entropy may quantify the amount of variation in intensity, color, texture, and the like within the shared region. Higher entropy may indicate richer image features that provide more reliable cues for alignment, while lower entropy may indicate uniform or featureless areas that may yield uncertain matches. In a non-limiting example, the processor 102 may compute overlap entropy 172 using Shannon entropy or similar formulations based on the distribution of pixel intensities within the overlap area. As used in this disclosure, "Shannon entropy" is a quantitative measure of the information content or uncertainty within an image region, based on the statistical distribution of pixel intensity values. Shannon entropy may express how much variability or randomness exists within the region, where higher entropy values indicate greater structural complexity and richer image detail, and lower entropy values indicate uniform or featureless areas. In another non-limiting example, an overlap region containing densely packed nuclei, high texture variation, may exhibit higher entropy and therefore produce a higher connectivity confidence score 168 than a blank glass region with uniform background intensity. As used in this disclosure, a "texture score" is a quantitative index that reflects the amount and distinctiveness of structural or morphological features present within an image region. Texture analysis may enable the processor 102 to assess whether an image region contains sufficient visual detail to support accurate alignment. The texture score 174 may be derived from spatial-frequency features, gray-level co-occurrence matrices (GLCM), or other image descriptors. In a non-limiting example, a high texture score 174 may correspond to a tissue-rich region with complex cellular architecture, such as densely packed glandular or epithelial structures. In another non-limiting example, a low texture score 174 may correspond to a smooth, homogeneous area such as mounting medium, clear background, or artifact-free glass.

With continued reference to FIG. 1, in a non-limiting example, processor 102 may be configured to generate a connectivity confidence score 168 for each pair of overlapping image fields of view as a function of the variance of residuals 170, overlap entropy 172, and texture score 174. The processor 102 may compute the variance of residuals 170 to quantify alignment stability, calculate overlap entropy 172 to assess feature richness, and evaluate the texture score 174 to determine visual distinctiveness. These parameters may be normalized and combined, using weighted summation, regression, or learned coefficients, into a single connectivity confidence score 168 that reflects the reliability of the connection between image tiles. As used in this disclosure, "learned coefficients" are numerical weighting values that have been determined or optimized by a computational learning process such as a machine learning or statistical training algorithm. These coefficients may represent the relative importance or influence of different input parameters within a model and are derived from training data rather than being manually assigned. The learned coefficients may allow the processor 102 to combine multiple measured features or metrics in a data-driven manner to improve accuracy, adaptability, and generalization across varying imaging conditions. Continuing, once the connectivity confidence score 168 is computed, the processor 102 may weight one or more local displacement equations 146 accordingly. Local displacement equations 146 derived from high-confidence regions, for example, those with low variance of residuals 170, high overlap entropy 172, and strong texture, may receive greater weighting in the alignment model, allowing them to exert stronger influence on the global mosaic 124 computation. Conversely, displacement equations from low-confidence regions, for example, smooth background or low-contrast areas, may be down-weighted or excluded to prevent propagation of alignment errors. In a non-limiting example, during a 40× magnification whole-slide imaging process, the processor 102 may compute a high connectivity confidence score 168, for example, 0.95 on a scale of 0 to 1, for an overlap between two adjacent image tiles containing rich glandular tissue, while assigning a lower score for example, 0.35 to an overlap region containing mostly background. The high-confidence region may therefore contribute more strongly to the least-squares alignment model, ensuring that tissue-rich connections dominate the optimization. By dynamically weighting displacement equations in this manner, the system may improve stitching precision, reduce noise from low-content regions, and enhance the overall structural integrity of the reconstructed global mosaic 124.

With continued reference to FIG. 1, processor 102 may be configured to identify a reference image 176 of the sequential image fields of view 108, wherein identifying the reference image 176 is a function of a stabilization protocol 178 and stabilize the global coordinates 122 assigned by the positioning model 116. As used in this disclosure, a "reference image" is a selected image field of view that serves as a fixed spatial or geometric anchor for aligning other image fields of view within a sequential imaging dataset. The reference image 176 may establish a stable coordinate origin or benchmark that the processor 102 uses to maintain positional consistency throughout the image acquisition and stitching process 126. The reference image 176 may be chosen based on image quality, structural richness, or positional stability, and it may represent the first image captured, the central region of the specimen, or a tile exhibiting minimal drift or distortion. In a non-limiting example, the processor 102 may designate a reference image 176 from the center of a tissue section that contains high texture contrast and distinct structural features, such as nuclei clusters or glandular outlines, allowing it to serve as a reliable anchor for alignment. In another non-limiting example, a reference image 176 may correspond to a high-confidence tile identified by the positioning model 116 as having the lowest displacement variance among its neighboring fields of view. As used in this disclosure, a "stabilization protocol" is a computational procedure that monitors, evaluates, and corrects spatial drift or geometric instability during sequential image acquisition or stitching. The stabilization protocol 178 ensures that the global coordinate framework remains consistent over time, preventing cumulative error propagation as additional fields of view are added to the global mosaic 124. The stabilization protocol 178 may include algorithms for motion correction, coordinate normalization, and adaptive reference reassignment. In a non-limiting example, the stabilization protocol 178 may evaluate incremental displacements between newly acquired image fields of view and previously established coordinates, detecting deviations that exceed a predefined tolerance such as more than about two pixels. When such drift is detected, the stabilization protocol 178 may either apply corrective coordinate shifts or select a new reference image 176 from among the most stable fields of view. In another non-limiting example, the stabilization protocol 178 may employ filtering or smoothing methods such as Kalman filtering or moving-average correction to stabilize coordinate estimates in real time.

With continued reference to FIG. 1, in a non-limiting example, processor 102 may be configured to identify a reference image 176 of the sequential image fields of view 108 based on a stabilization protocol 178 and use that reference to stabilize the global coordinates 122 assigned by the positioning model 116. The stabilization protocol 178 may continuously assess displacement consistency and motion variance across all captured fields of view, selecting the image tile or region that exhibits the lowest positional drift and highest correlation to neighboring fields as the reference image 176. Once identified, the processor 102 may fix the global coordinates 122 of this reference image 176 as the anchor point within the global coordinate framework. Subsequent fields of view may be aligned relative to the reference image 176, ensuring that all coordinate adjustments preserve the geometric stability of the overall mosaic. In a non-limiting example, during a 40× magnification whole-slide scan, the processor 102 may designate the central tissue tile of the first scan row as the reference image 176 and monitor cumulative coordinate drift during acquisition. If the stabilization protocol 178 detects systematic downward drift in later-acquired regions, it may adjust the global coordinate transformation matrix to preserve alignment relative to the fixed reference image 176. This process may ensure that the global mosaic 124 remains spatially coherent, geometrically stable, and diagnostically accurate across the entire reconstructed slide. In a non-limiting example, certain fields of view (FOVs) within the sequence of acquired images may be designated as anchor points to stabilize global positioning during the stitching and alignment process. These anchor points may serve as fixed spatial references that the processor 102 uses to maintain consistency and prevent drift in the global coordinate framework as additional images are captured and integrated into the mosaic. The selection of anchor points may be performed automatically by the system based on image stability, feature richness, or positional reliability, or it may be predefined according to the scanning pattern or specimen structure. Each anchor point may correspond to an FOV that exhibits high image quality and low displacement variance, such as a tile containing dense tissue features, strong contrast, and minimal motion artifacts. These anchor FOVs may be distributed strategically across the slide to provide geometric stability across both local and global regions. The processor 102 may assign fixed or semi-fixed global coordinates 122 to each anchor point and adjust the positioning of other FOVs relative to them, ensuring that the global coordinate model remains stable throughout acquisition. In a non-limiting example, during a 40× magnification whole-slide imaging operation, the processor 102 may automatically select one FOV every fifty images as an anchor point. Each anchor point may be used as a spatial benchmark to correct for gradual stage drift or cumulative displacement error. As the scan progresses, the processor 102 may compare the measured positions of new FOVs against nearby anchor points and apply coordinate corrections if deviations exceed a predefined threshold 130 such as more than about one pixel. Without limitation, by designating anchor FOVs in this manner, the apparatus 100 may effectively constrain global drift, maintain spatial continuity between regions, and ensure that all image tiles remain properly aligned within the global mosaic 124. This approach may improve the robustness of real-time stitching, allowing large-scale pathology slides or fragmented tissue specimens to be reconstructed with high geometric accuracy and minimal distortion.

With continued reference to FIG. 1, processor 102 may be configured to post-process, using a concurrent post-processing module 180, the global mosaic 124, wherein post-processing the global mosaic 124 comprises generating a panorama 182 of the global mosaic 124. As used in this disclosure, "post-process" is a computational operation performed after the initial image acquisition and stitching stages. Without limitation, the post-process may be to refine, enhance, or finalize the global mosaic 124 for visualization, analysis, or storage. Post-processing may include operations such as color correction, illumination normalization, artifact removal, focus blending, image compression, dynamic range adjustment, and the like. These steps may ensure that the reconstructed image achieves consistent quality, seamless appearance, and diagnostic clarity. In a non-limiting example, the processor 102 may post-process a stitched whole-slide image to equalize brightness across tile boundaries and remove residual stitching artifacts prior to visualization. In another non-limiting example, post-processing may include generating compressed image pyramids or multi-resolution layers for efficient viewing and analysis. As used in this disclosure, a "concurrent post-processing module" is a computational subsystem configured to perform post-processing tasks simultaneously with ongoing image acquisition or stitching operations. The concurrent post-processing module 180 may enable the system to process data in parallel, ensuring that visualization or enhancement tasks occur in real time without delaying the scanning workflow. This may allow continuous throughput while maintaining image quality. In a non-limiting example, the concurrent post-processing module 180 may perform image blending and illumination correction on previously stitched regions while new image tiles are being acquired and aligned. In another non-limiting example, the post-processing module may run on a separate processing thread or GPU pipeline that executes enhancement and rendering operations concurrently with the main alignment process. As used in this disclosure, a "panorama" is a wide-field composite image generated by merging multiple overlapping image fields of view into a single, continuous representation of the entire specimen or region of interest. The panorama 182 may provide a unified visual perspective of the global mosaic 124, allowing seamless navigation and inspection across the complete tissue area. In a non-limiting example, the panorama 182 may be a high-resolution digital reconstruction of a whole pathology slide that spans the full scanned area without visible seams or discontinuities. In another non-limiting example, a panorama 182 may include a low-resolution overview image derived from the global mosaic 124 that allows users to navigate quickly between regions of interest for detailed analysis.

With continued reference to FIG. 1, in a non-limiting example, processor 102 may be configured to post-process the global mosaic 124 using a concurrent post-processing module 180, wherein post-processing the global mosaic 124 comprises generating a panorama 182 of the reconstructed specimen. As the processor 102 completes stitching of each segment of the slide, the concurrent post-processing module 180 may immediately begin applying image enhancement operations such as local intensity normalization, contrast adjustment, boundary smoothing, and the like. This concurrent execution may allow the apparatus 100 to prepare finalized image layers while additional fields of view are still being acquired. In a non-limiting example, once the global coordinates 122 of all stitched tiles have been established, the concurrent post-processing module 180 may generate a panorama 182 by compositing the entire global mosaic 124 into a continuous image. The post-processing module may blend overlapping boundaries using feathering or gradient-domain fusion to eliminate visible seams and may generate multi-resolution image pyramids for smooth zooming and viewing. In another non-limiting example, during a 40× magnification whole-slide scan, the processor 102 may continuously render a live panorama 182 that updates as each new image tile is integrated into the global mosaic 124, allowing real-time visualization of the slide as it is being scanned. Without limitation, the concurrent post-processing module 180 may enhance workflow efficiency, reduce overall processing time, and provide immediate access to a high-quality panoramic image of the entire specimen.

With continued reference to FIG. 1, the at least a processor 102 may be configured to display one or more of the global mosaic 124, the stitched slide image 140, the panoramic reconstruction and the like, using a user interface. Without limitation, the user interface may provide real-time or near real-time visualization of the reconstructed image data, enabling interactive navigation, zooming, annotation, or measurement within the digital slide environment. As used in this disclosure, a "user interface" is a collection of hardware and/or software components configured to enable interaction between a user and a computing device, wherein the user interface facilitates the presentation of data to the user and the reception of input from the user. The user interface may include, without limitation, graphical user interfaces, command-line interfaces, application programming interfaces, voice-based interfaces, haptic interfaces, or augmented reality interfaces. A "graphical user interface," as used herein, is a graphical form of user interface that allows users to interact with electronic devices. In some embodiments, GUI may include icons, menus, other visual indicators or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pull-down menu may appear. A menu may include a context menu that appears only when the user performs a specific action. An example of this is pressing the right mouse button. When this is done, a menu may appear under the cursor. Files, programs, web pages and the like may be represented using a small picture in a graphical user interface. For example, links to decentralized platforms as described in this disclosure may be incorporated using icons. Using an icon may be a fast way to open documents, run programs etc. because clicking on them yields instant access.

With continued reference to FIG. 1, in an embodiment, the graphical user interface and an event handler may operate together to enable seamless interaction between the user and the apparatus 100. The GUI serves as the visual and interactive layer through which the user engages with the apparatus 100, presenting elements such as buttons, sliders, input fields, and informational displays. The event handler, on the other hand, functions as the underlying mechanism that monitors and responds to user interactions with the GUI. For example, when a user clicks a button on the GUI to request an explanation of a concept, the event handler may detect the click event, identify its context, and trigger the appropriate processes within the apparatus 100 to generate a tailored response. This interplay may ensure dynamic and responsive system behavior, as the event handler processes various input events such as clicks, taps, keystrokes, or voice commands, and relays these inputs to the relevant system components. The GUI subsequently updates to reflect the system's responses, such as displaying output, modifying visual elements, or providing real-time feedback. Together, the GUI and event handler create an intuitive and interactive experience, bridging user actions and system functionality to achieve efficient and personalized outcomes.

With continued reference to FIG. 1, an "event handler," as used in this disclosure, is a module, data structure, function, and/or routine that performs an action in response to an event. For instance, and without limitation, an event handler may record data corresponding to user selections of previously populated fields such as drop-down lists and/or text auto-complete and/or default entries, data corresponding to user selections of checkboxes, radio buttons, or the like, potentially along with automatically entered data triggered by such selections, user entry of textual data using a keyboard, touchscreen, speech-to-text program, or the like. Event handler may generate prompts for further information, may compare data to validation rules such as requirements that the data in question be entered within certain numerical ranges, and/or may modify data and/or generate warnings to a user in response to such requirements.

With continued reference to FIG. 1, as used in this disclosure, a "visual element" is a component or feature within a system, display, or interface that conveys information through visual means. In a non-limiting example, the visual element may include text, images, icons, shapes, colors, and/or other graphical components designed to be perceived by the user. In a non-limiting example, the visual element may aid in communication, navigation, and/or interaction with the system. Without limitation, the visual element may be used to enhance user experience, guide behavior, and/or represent data visually in an intuitive or informative way. A visual element may include data transmitted to display device, client device, and/or graphical user interface. In some embodiments, visual element may be interacted with. For example, visual element may include an interface, such as a button or menu. In some embodiments, visual element may be interacted with using a user device such as a smartphone, tablet, smartwatch, or computer.

With continued reference to FIG. 1, in an embodiment, the apparatus 100 and or the downstream device may include a data structure. As used in this disclosure, "data structure" is a way of organizing data represented in a specialized format on a computer configured such that the information can be effectively presented in a graphical user interface. In some cases, the data structure includes any input data. In some cases, the data structure contains data and/or rules used to visualize the graphical elements within a graphical user interface. In some cases, the data structure may include any data described in this disclosure. In some cases, the data structure may be configured to modify the graphical user interface, wherein data within the data structure may be represented visually by the graphical user interface. In some cases, the data structure may be continuously modified and/or updated by processor 102, wherein elements within graphical user interface may be modified as a result. In some cases, processor 102 may be configured to transmit display device and or the downstream device the data structure. Transmitting may include, and without limitation, transmitting using a wired or wireless connection, direct, or indirect, and between two or more components, circuits, devices, systems, and the like, which allows for reception and/or transmittance of data and/or signal(s) therebetween. Data and/or signals there between may include, without limitation, electrical, electromagnetic, magnetic, video, audio, radio, and microwave data and/or signals, combinations thereof, and the like, among others. Processor 102 may transmit the data described above to a database wherein the data may be accessed from the database. Processor 102 may further transmit the data above to a display device, client device, or another computing device. The data structure may serve as the organizational framework that stores, retrieves, and manages data required for processing events and updating the GUI. The data structure may act as a bridge between the user's input, captured by the event handler, and the output displayed on the GUI, ensuring that information is handled efficiently and accurately throughout the interaction. For example, without limitation, when a user interacts with a dropdown menu in the GUI to select a topic, the event handler may capture this input and accesses a data structure. The data structure may retrieve the relevant information such as, text explanations, videos, or interactive exercises, and passes it back to the event handler, which may then trigger the appropriate updates to the GUI. In another embodiment, the data structure may also maintain the state of the system, tracking user progress, preferences, and session history. For instance, without limitation, a hash table may store user specific configurations which the event handler references when processing interactions. The GUI may then dynamically adapt to display content aligned with these configurations. This integration may ensure that user inputs are seamlessly translated into meaningful system outputs, with the data structure enabling rapid access, consistency, and scalability throughout the process. As used in this disclosure, a "hash table" is a data structure that stores data in a way that allows for fast retrieval, insertion, and deletion of elements. The hash table may organize data into key-value pairs, where each key is unique and used to identify its corresponding value. A hash table may use a hash function to compute an index, or hash code, from the key, which determines where the key-value pair is stored within an array or list.

With continued reference to FIG. 1, as used in this disclosure, an "interactive element" is a component or feature within a graphical user interface (GUI) that allows users to perform actions, provide input, or engage with the apparatus 100. Interactive elements may be designed to facilitate two-way communication between the user and the system, enabling the user to influence the behavior of the apparatus 100 or obtain feedback in response to their actions. Examples of interactive elements may include buttons, dropdown menus, sliders, checkboxes, input fields, and hyperlinks. More advanced interactive elements may include drag-and-drop interfaces, interactive diagrams, or dynamically updating content areas that respond to user actions in real time. The interactive elements may enhance user engagement by providing intuitive and responsive mechanisms for interacting with the system. Interactive elements may operate by responding to user actions such as clicks, taps, swipes, or keyboard inputs, and triggering predefined system behaviors or processes. The execution of the interactive elements may require a combination of front-end and back-end technologies that work together to provide seamless functionality and user interaction. On the front end, technologies such as HTML and CSS may define the structure, appearance, and layout of the interactive elements, while JavaScript may enable dynamic functionality. For example, without limitation, JavaScript may detect when the user clicks a button and trigger actions or animations. Front-end frameworks like React, Angular, or Vue.js may further enhance development by offering reusable components and efficient rendering mechanisms. On the back end, the system may process the user's input, retrieve the necessary data, and communicate with the front end to provide an appropriate response. APIs may act as a bridge between the front end and back end, facilitating data transfer, such as sending a user's form submission to the server and retrieving processed results. Server-side logic, implemented using languages like Python, Java, or Node.js, may handle input processing and return relevant data. Additional supporting technologies may ensure the smooth operation of interactive elements. Event listeners, for instance, may continuously monitor for specific actions like mouse clicks or text entries, executing code when such events are detected. Efficient data structures, such as hash tables or dictionaries, may store interactive state data, such as user preferences or settings, for quick access and updates. Databases, including MySQL or MongoDB, may manage and store the data required for interactive features, such as user profiles or historical activity. Communication technologies may also help maintain the responsiveness of interactive elements. AJAX (Asynchronous JavaScript and XML) may allow the front end to update portions of a web page without requiring a full page reload, enhancing responsiveness. WebSockets may provide real-time interaction capabilities, such as live chats or collaborative tools, by enabling persistent communication between the client and the server. Without limitation, the apparatus 100 may include one or more APIs. As used in this disclosure, an "application programming interface (API)" is a set of defined protocols, tools, and methods that allow different software applications, systems, or components to communicate and interact with each other. An API may act as an intermediary that enables a client application, such as a user-facing app, to send requests to a server or service and receive the necessary responses, facilitating seamless integration and functionality across diverse systems.

With continued reference to FIG. 1, as used in this disclosure, "downstream device" is a device that accesses and interacts with apparatus 100. For instance, and without limitation, downstream device may include a remote device and/or apparatus 100. In a non-limiting embodiment, downstream device may be consistent with a computing device as described in the entirety of this disclosure. Without limitation, the downstream device may include a display device. As used in this disclosure, a "display device" refers to an electronic device that visually presents information to the entity. In some cases, display device may be configured to project or show visual content generated by computers, video devices, or other electronic mechanisms. In some cases, display device may include a liquid crystal display (LCD), a cathode ray tube (CRT), a plasma display, a light emitting diode (LED) display, and any combinations thereof. In a non-limiting example, one or more display devices may vary in size, resolution, technology, and functionality. Display device may be able to show any data elements and/or visual elements as listed above in various formats such as, textural, graphical, video among others, in either monochrome or color. Display device may include, but is not limited to, a smartphone, tablet, laptop, monitor, tablet, and the like. Display device may include a separate device that includes a transparent screen configured to display computer generated images and/or information. In some cases, display device may be configured to present a graphical user-interface (GUI) to a user, wherein a user may interact with a GUI. In some cases, a user may view a GUI through display. Additionally, or alternatively, processor 102 be connected to display device. In one or more embodiments, transmitting the global mosaic 124, stitched slide image 140, and/or panoramic reconstruction may include displaying the global mosaic 124, stitched slide image 140, and/or panoramic reconstruction at display device using a visual interface.

With continued reference to FIG. 1, in a non-limiting example, the user interface may display the panoramic global mosaic 124 as it is being generated by the stitching and post-processing modules, allowing an operator to monitor progress, verify alignment accuracy, and assess image quality. The interface may include visualization tools that permit the user to dynamically pan across the specimen, adjust contrast or brightness, and overlay diagnostic or analytical data. In another non-limiting example, the user interface may display individual fields of view alongside their computed global coordinates 122, enabling inspection of how each tile contributes to the overall mosaic structure. In another non-limiting example, the processor may display real-time status indicators such as stitching confidence metrics, error thresholds, or processing speed, allowing users to assess system performance during acquisition. Once post-processing is complete, the user interface may display the finalized high-resolution digital slide as a fully interactive panorama 182, which may support annotation layers, measurement tools, or automated analysis overlays. Without limitation, the system may allow users to visualize the complete reconstructed slide or selected portions thereof in a seamless and responsive environment, enhancing workflow efficiency, quality assurance, and diagnostic precision in digital pathology and related imaging applications.

With continued reference to FIG. 1, the apparatus 100 is an improvement on existing technology for multiple reasons. In a non-limiting embodiment, the apparatus 100 is an improvement because it performs inline global positioning and stitching during slide acquisition rather than after data capture, thereby eliminating the delay associated with post-acquisition processing. Continuing, by continuously computing global coordinates 122 in real time, the apparatus 100 may enable immediate feedback, faster reconstruction, and more efficient data throughput. The apparatus 100 is an improvement because it integrates a concurrent post-processing module 180 that operates in parallel with image acquisition. This configuration may allow blending, tiling, illumination correction, and panorama 182 generation to occur as soon as image data becomes available, significantly reducing total whole slide image generation time. In another non-limiting embodiment, the apparatus 100 is an improvement because it incorporates adaptive error monitoring and correction, detecting stitching discrepancies during acquisition rather than afterward. When an alignment error exceeds a predefined threshold 130, the system may automatically trigger a fallback model 132, such as a graph-based optimization process, ensuring that the final mosaic maintains high positional accuracy without requiring manual intervention. The apparatus 100 may further represent an improvement through its use of a hybrid control mechanism, which intelligently selects between linear and graph-based alignment methods depending on image connectivity, displacement variance, or local confidence metrics. This hybrid adaptability allows the system to maintain geometric precision even in challenging imaging scenarios, such as fragmented tissue regions or partially connected samples. Additionally and/or alternatively, the apparatus 100 may improve overall diagnostic workflow by providing real-time visualization through a user interface that displays the reconstructed mosaic as it is generated. This enables operators to verify image quality, confirm alignment accuracy, and identify potential issues without pausing the acquisition process. Collectively, these capabilities may allow the apparatus 100 to enhance imaging efficiency, minimize processing delays, and maintain or exceed the spatial accuracy of conventional systems, resulting in a faster, more robust, and more intelligent whole slide imaging platform as described herein.

Figure 2:
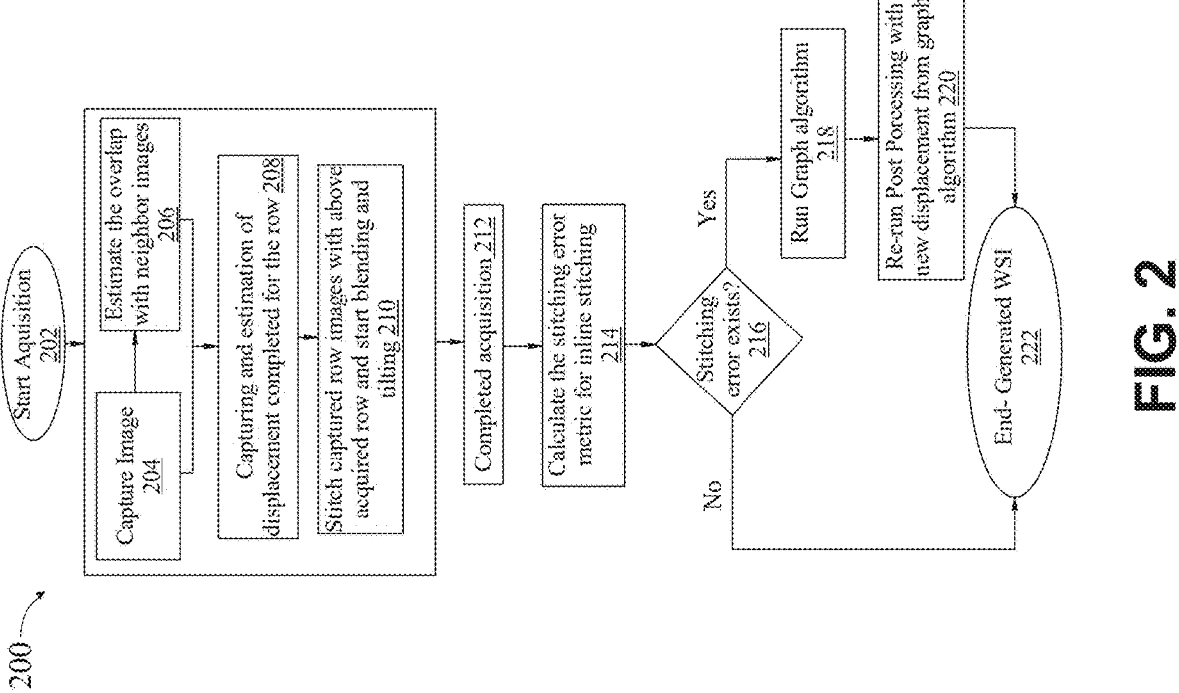
FIG. 2 is an exemplary illustration depicting a flowchart of a process to generate a whole slide image.

Referring now to FIG. 2, an exemplary illustration 200 of a flowchart of a process to generate a whole slide image is depicted. In a non-limiting embodiment, the process may include several sequential steps executed by the apparatus 100 to perform inline image acquisition, positioning, stitching, and post-processing operations in real time. In an embodiment, the exemplary illustration 200 may include Start Acquisition 202. Without limitation, Start Acquisition 202 may include initializing the imaging sequence, activating the stage control, and setting imaging parameters such as focus depth, illumination intensity, and scan boundaries. The processor may establish communication with the image acquisition engine 106, verify calibration settings, and prepare the optical and mechanical subsystems for continuous scanning of the specimen. In an embodiment, the exemplary illustration 200 may include Capture Image 204. Without limitation, Capture Image 204 may include acquiring an image field of view (FOV) from the specimen using the image acquisition engine 106. The processor may record the captured FOV, tag it with positional metadata, and forward it to the processing pipeline for immediate analysis. This step may involve controlling the stage movement, synchronizing the camera exposure, and maintaining focus to ensure high-quality image capture during continuous scanning. In an embodiment, the exemplary illustration 200 may include Estimate the Overlap with Neighbor Images 206. Without limitation, Estimate the Overlap with Neighbor Images 206 may include determining the overlapping regions between the newly captured FOV and adjacent previously acquired images. The processor may use correlation-based or feature-matching algorithms to measure relative displacement, identify matching features, and quantify the degree of overlap to support accurate stitching. In an embodiment, the exemplary illustration 200 may include Capturing and Estimation of Displacement Completed for the Row 208. Without limitation, this step may include completing the acquisition of all FOVs in a given scan row and computing the relative displacements between all neighboring images in that row. The processor may confirm that the displacement information is consistent and ready for integration into the positioning model. In an embodiment, the exemplary illustration 200 may include Stitch Captured Row Images with Above Acquired Row and Start Blending and Tiling 210. Without limitation, this step may include aligning the newly captured row of FOVs with the previously acquired row to ensure global spatial continuity. The processor may begin blending intensity values across overlapping regions and initiate tiling to build the panoramic mosaic incrementally while acquisition continues. In an embodiment, the exemplary illustration 200 may include Completed Acquisition 212. Without limitation, this step may include determining that all required FOVs for the entire slide have been captured. The processor may finalize acquisition operations and transition the workflow from image capture to validation and post-processing. In an embodiment, the exemplary illustration 200 may include Calculate the Stitching Error Metric for Inline Stitching 214. Without limitation, this step may include computing quantitative error metrics, such as residual offsets, displacement variance, or correlation mismatch values, to evaluate the accuracy of the inline stitching results. The processor may compare these error values against predefined thresholds to determine whether the stitching process is within acceptable limits. In an embodiment, the exemplary illustration 200 may include Stitching Error Exists 216. Without limitation, this decision step may include determining whether the calculated stitching error exceeds the acceptable tolerance level. If the error remains within range, the process proceeds to finalization; if not, corrective actions may be triggered. In an embodiment, the exemplary illustration 200 may include Run Graph Algorithm 218. Without limitation, this step may include executing a graph-based optimization procedure as a fallback model to correct global positional inconsistencies. The processor may construct a connectivity graph representing all FOVs and optimize node positions to minimize global stitching error across the entire slide. In an embodiment, the exemplary illustration 200 may include Re-run Post-Processing with New Displacement from Graph Algorithm 220. Without limitation, this step may include updating the global mosaic using the refined displacements generated by the graph algorithm and reapplying blending, tiling, and rendering operations to ensure seamless continuity. In an embodiment, the exemplary illustration 200 may include End-Generated WSI 222. Without limitation, this step may include finalizing the reconstructed whole slide image (WSI), saving the completed panoramic image to storage, and displaying it through the user interface for visualization, verification, or analysis. Without limitation, through this sequence of operations, the process may enable inline acquisition, real-time positioning, and dynamic correction of alignment errors, resulting in an accurate and high-quality digital slide, as described herein.

Figure 3:
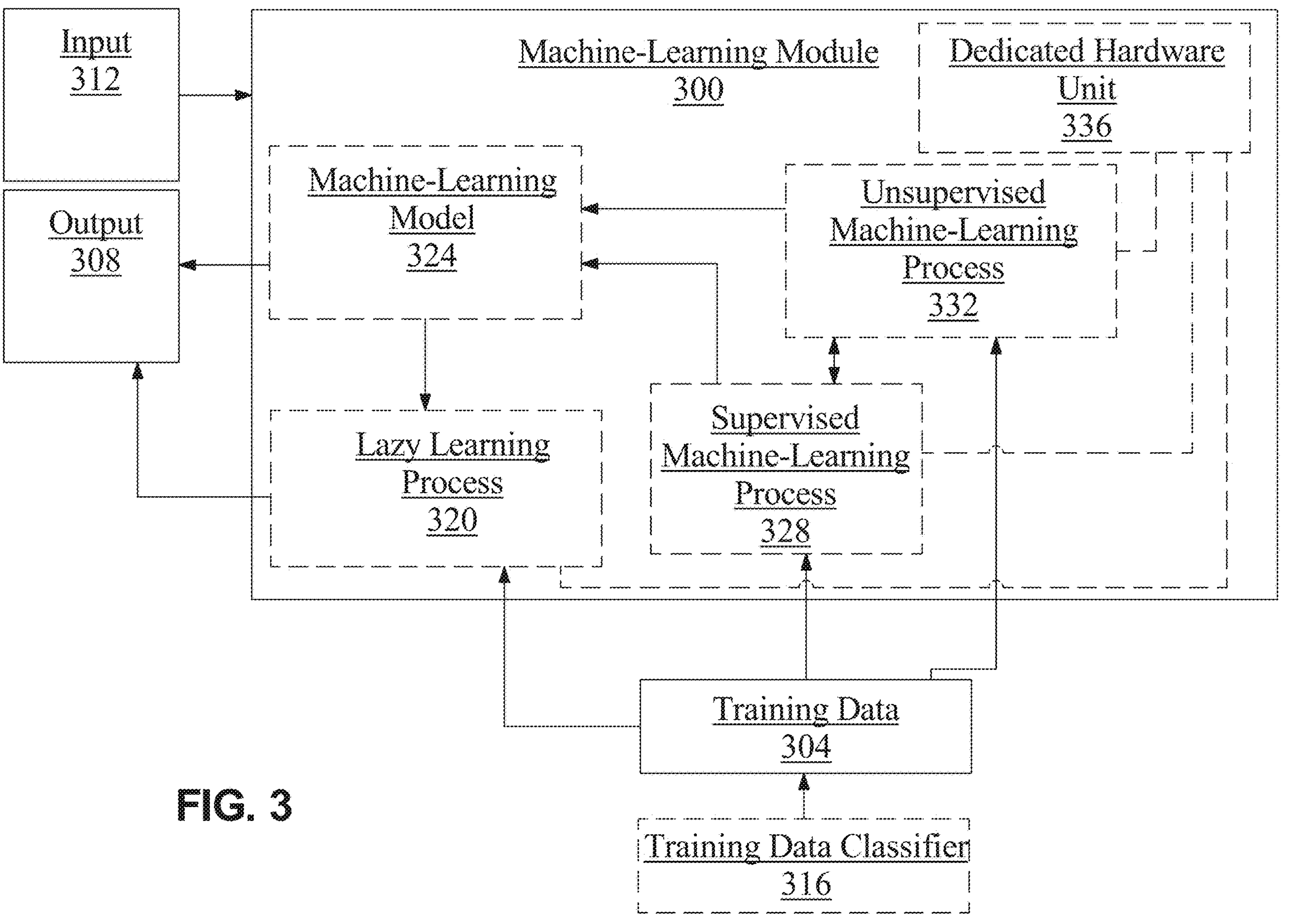
FIG. 3 is a block diagram of an exemplary machine-learning module.

Referring now to FIG. 3, an exemplary embodiment of a machine-learning module 300 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm instantiated in hardware or software logic, data structures, and/or functions that will be performed by a computing device/module to produce outputs 308 given data provided as inputs 312; this is in contrast to a non-machine learning software program where the commands to be executed are determined in advance by a user and written in a programming language.

Still referring to FIG. 3, "training data," as used herein, is data containing correlations that a machine-learning process may use to model relationships between two or more categories of data elements. For instance, and without limitation, training data 304 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; for instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure. In a non-limiting illustrative example, the input data may include image-derived features extracted from overlapping fields of view such as pixel intensity distributions, texture descriptors, local feature maps, displacement vectors, variance of residuals, overlap entropy values, and connectivity confidence scores. The machine-learning module 300 may process these inputs to learn patterns that indicate alignment quality, tissue connectivity, or positional drift during whole slide imaging. The corresponding output data may include predicted global coordinate corrections, confidence-weighting factors for local displacement equations, error threshold adjustments, or classification labels indicating whether a given image region requires fallback correction. For instance, the training data may associate high-entropy, texture-rich overlaps with strong confidence scores and low alignment error, while associating uniform or low-texture regions with higher uncertainty and larger predicted displacement correction values. In another non-limiting example, the input data may consist of metadata streams generated during acquisition such as stage position, focus metrics, illumination intensity, and estimated displacement vectors, while the output data may include optimized coordinate predictions, adaptive weighting parameters for least-squares minimization, or real-time adjustment recommendations for maintaining stitching continuity. In another non-limiting example, the machine-learning module 300 may receive as input a sequence of local foreground and background segmentation masks and produce as output region classification data identifying disconnected tissue islands or biopsy fragments that require independent local alignment. Through these learned input-output relationships, the module may continuously refine its predictions and dynamically improve the accuracy, speed, and robustness of inline stitching, global positioning, and post-processing operations as described herein.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 300 may generate a classifier using a classification algorithm, defined as a processes whereby a computing device and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to a defined subset or sub-population of imaging conditions or specimen characteristics for which specialized processing or analysis is beneficial. The sub-population may include specific categories of tissue morphology, imaging quality conditions, or acquisition parameters that influence alignment performance or feature extraction accuracy. In a non-limiting illustrative example, the training data classifier 316 may classify image tiles or displacement samples according to tissue type, staining characteristics, or structural density, such as differentiating epithelial, stromal, or necrotic regions. This classification may allow the machine-learning module to tailor its displacement prediction and weighting functions to the visual complexity of each tissue type.

Still referring to FIG. 3, Computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A)P(A)$ ÷P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 3, Computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 3, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 3, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 3, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 3, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 3, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 3, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 3, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 3, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 3, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max}: X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation σ of a set or subset of values:

$$X_{new} = \frac{X - X_{mean}}{\sigma}.$$

Scaling may be performed using a median value of a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 3, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning models 324. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include image feature maps, displacement vectors, and overlap statistics as inputs, and predicted global coordinate corrections, confidence weights, or alignment accuracy scores as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

With further reference to FIG. 3, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 3, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 332 may not require a response variable; unsupervised processes 332 may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g., a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including, without limitation, support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 3, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 3, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 3, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 3, one or more processes or algorithms described above may be performed by at least a dedicated hardware unit 336. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 336 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 336 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 336 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 4:
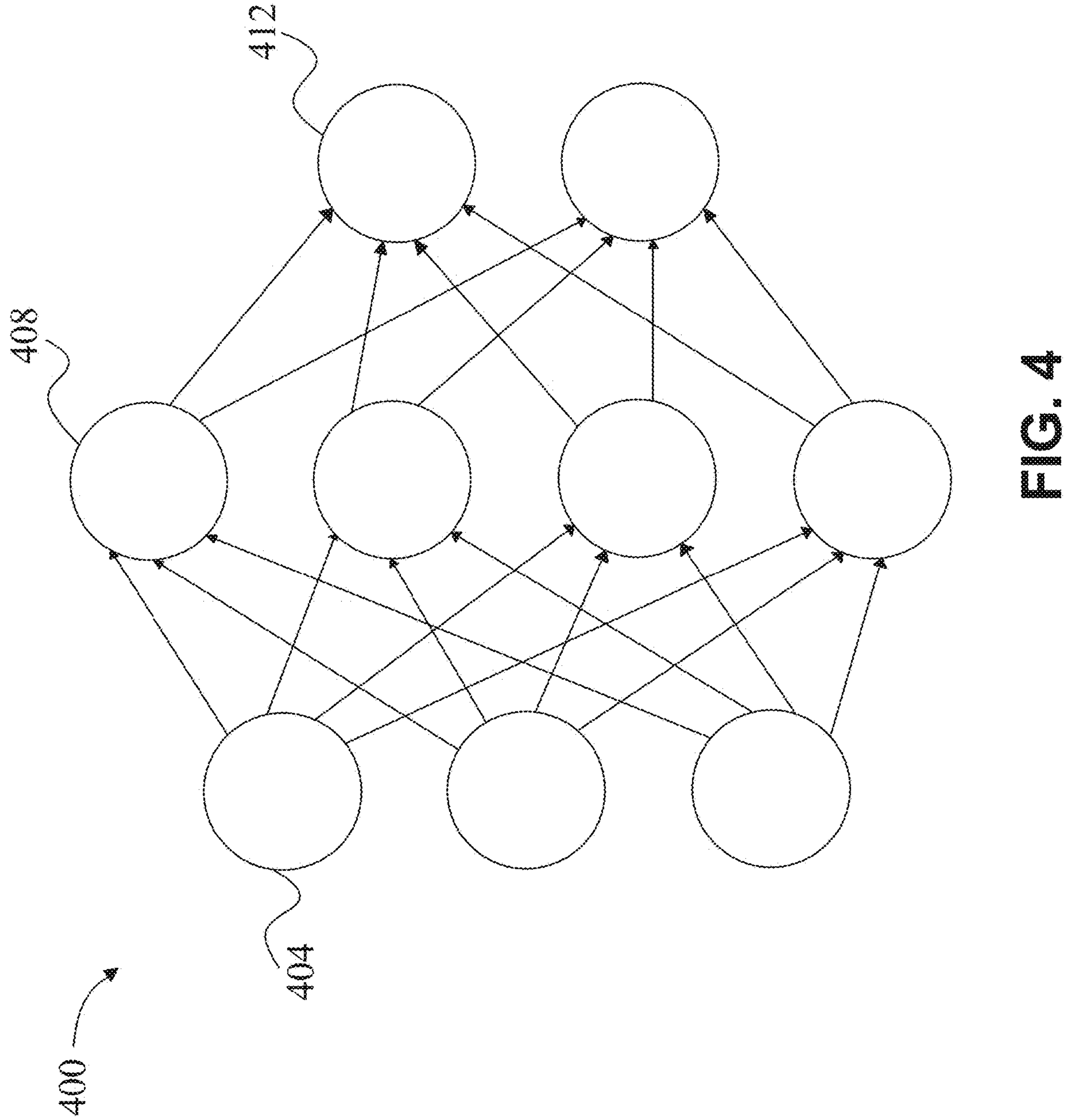
FIG. 4 is a diagram of an exemplary embodiment of a neural network.

Referring now to FIG. 4, an exemplary embodiment of neural network 400 is illustrated. A neural network 400 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 404, one or more intermediate layers 408, and an output layer of nodes 412. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 5:
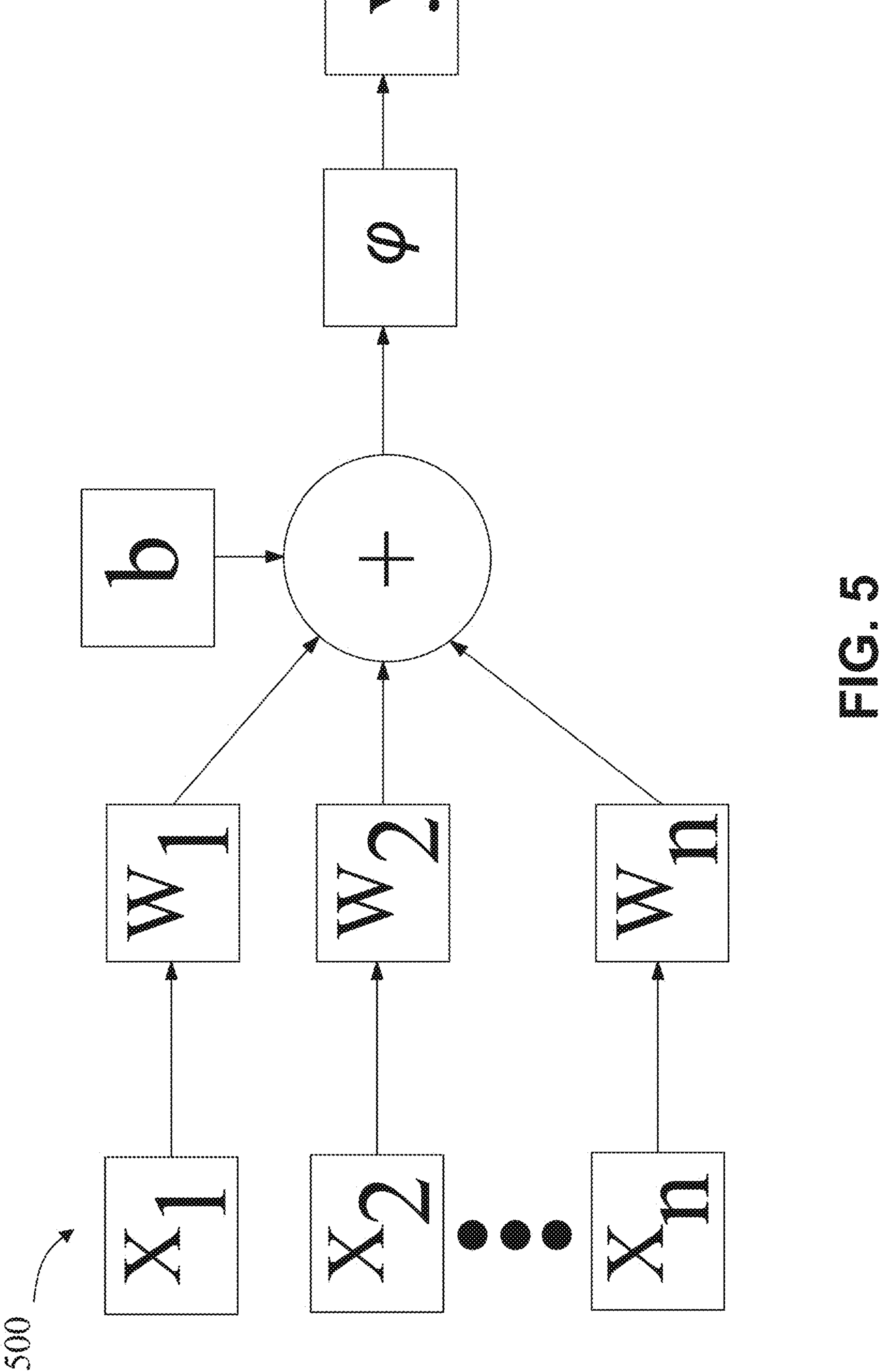
FIG. 5 is a diagram of an exemplary embodiment of a node of a neural network.

Referring now to FIG. 5, an exemplary embodiment 500 of a node of a neural network is illustrated. A node may include, without limitation, a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x \text{ for } x \geq 0 \\ \alpha(e^x - 1) \text{ for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) \text{ for } x < 0 \\ x \text{ for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function p, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 6:
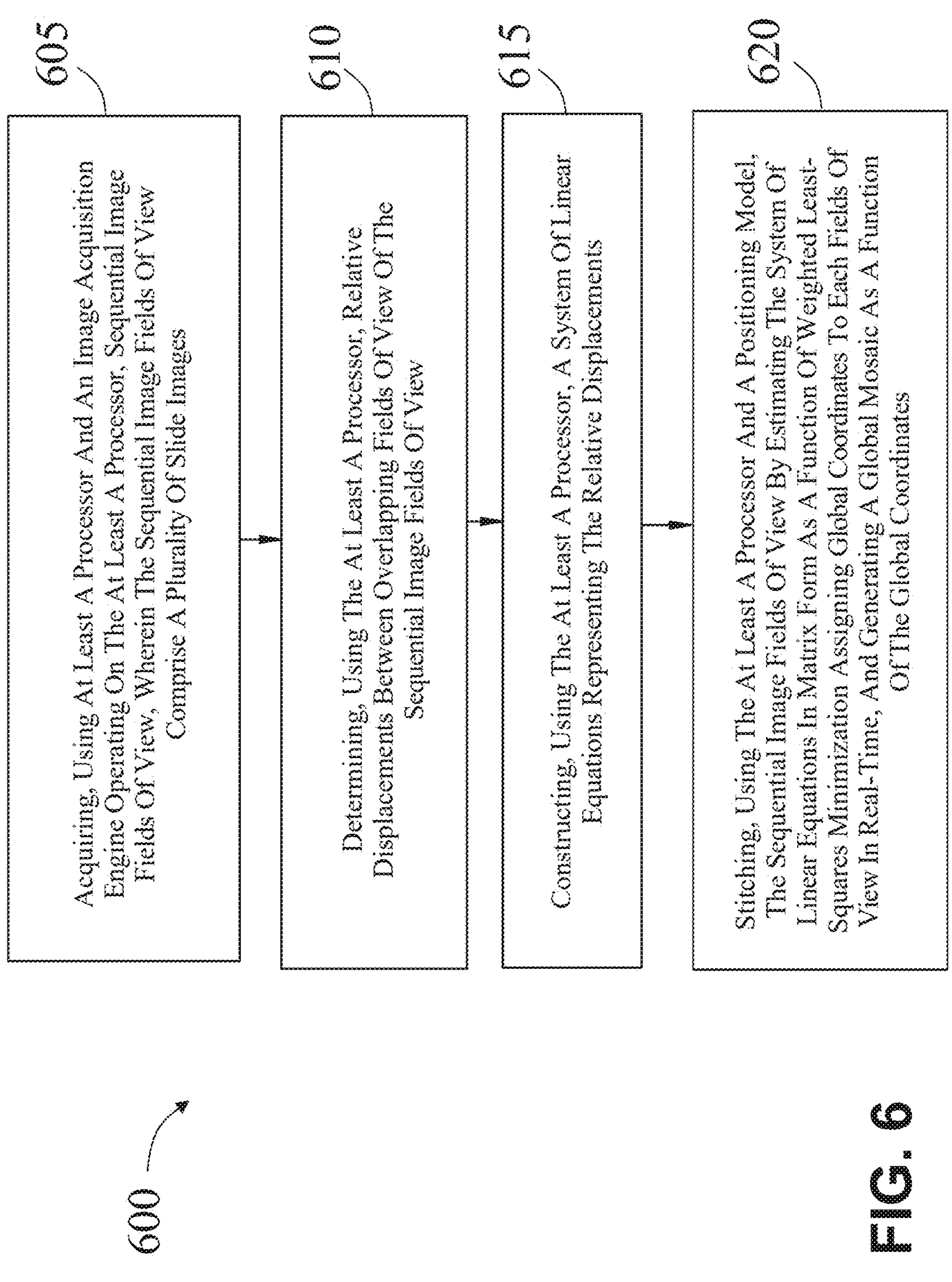
FIG. 6 is a block diagram of an exemplary method of real-time global positioning of images.

Referring now to FIG. 6, a flow diagram of an exemplary method 600 for real-time global positioning of images is illustrated. At step 605, method 600 includes acquiring, using at least a processor and an image acquisition engine operating on the at least a processor, sequential image fields of view, wherein the sequential image fields of view comprise a plurality of slide images. This may be implemented as described and with reference to FIGS. 1-5.

Still referring to FIG. 6, at step 610, method 600 includes determining, using at least a processor, relative displacements between overlapping fields of view of the sequential image fields of view. This may be implemented as described and with reference to FIGS. 1-5.

Still referring to FIG. 6, at step 615, method 600 includes constructing, using the at least a processor, a system of linear equations representing the relative displacements. This may be implemented as described and with reference to FIGS. 1-5.

Still referring to FIG. 6, at step 620, method 600 includes stitching, using a positioning model, the sequential image fields of view by estimating the system of linear equations in matrix form as a function of weighted least-squares minimization, assigning global coordinates to each fields of view in real-time, and generating a global mosaic as a function of the global coordinates. In an embodiment, the at least a processor may be further configured to monitor a stitching process, identify a stitching error of the sequential image fields of view, wherein the stitching error exceeds a predefined threshold, and compensate, using a fallback model, the stitching error of the stitching process. In an embodiment, the at least a processor may be further configured to instantiate a hybrid controller, wherein the hybrid controller selects the fallback model as a function of a coherence datum, wherein the fallback model comprises a graph-based algorithm. In an embodiment, the at least a processor may be further configured to segment a slide image of the plurality of slide images into a local foreground region and an isolated background region, stitch, using one or more local displacement equations, each local region into the global mosaic, and compensate, using the fallback model, the stitching error of the global mosaic. In an embodiment, the local foreground region may correspond to a disconnected tissue island. In an embodiment, the at least a processor may be further configured to adjust, using a displacement continuity protocol, upstream global coordinates of previously acquired fields of view of the sequential image fields of view, wherein the previously acquired fields of view comprises a partially connected pattern. In an embodiment, the at least a processor may be further configured to identify a lower connected segment that deviates from an upper segment and adjust, using constrained least-squares optimization, a row-wise position, wherein adjusting the row-wise position comprises an upward adjustment of the lower connected segment. In an embodiment, the at least a processor may be further configured to generate a connectivity confidence score as a function of variance of residuals, overlap entropy, and texture score of the sequential image fields of view and weight, using the connectivity confidence score, the one or more local displacement equations. In an embodiment, the at least a processor may be further configured to identify a reference image of the sequential image fields of view, wherein identifying the reference image is a function of a stabilization protocol, and stabilize the global coordinates assigned by the positioning model. In an embodiment, the at least a processor may be further configured to post-process, using a concurrent post-processing module, the global mosaic, wherein post-processing the global mosaic comprises generating a panorama of the global mosaic. This may be implemented as described and with reference to FIGS. 1-5.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
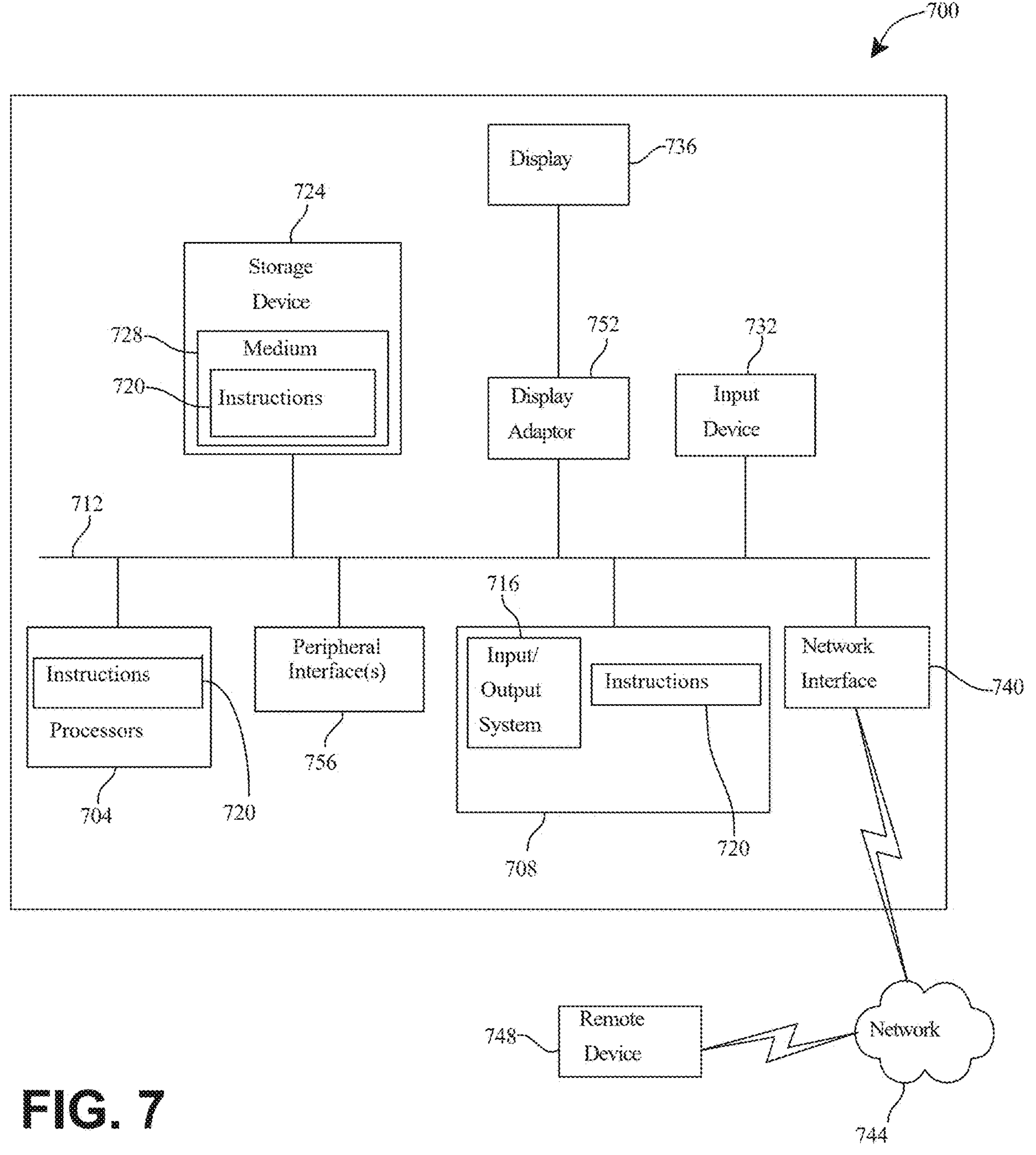
FIG. 7 is a block diagram of a computing system that can be used to implement any one or more of the methodologies disclosed herein and any one or more portions thereof.

FIG. 7 shows a diagrammatic representation of one embodiment of computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display device 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for real-time global positioning of images, wherein the apparatus comprises:

at least a computing device, wherein the at least a computing device comprises:

a memory; and at least a processor communicatively connected to the memory, wherein the memory contains instructions configuring the at least a processor to:

acquire, using an image acquisition engine, sequential image fields of view, wherein the sequential image fields of view comprise a plurality of slide images;

determine relative displacements between overlapping fields of view of the sequential image fields of view;

construct a system of linear equations representing the relative displacements;

stitch, using a positioning model, the sequential image fields of view by:

estimating the system of linear equations in matrix form as a function of weighted least-squares minimization;

assigning global coordinates to each field of view in real-time; and generating a global mosaic as a function of the global coordinates;

monitor the stitching of the sequential image fields of view;

identify a stitching error of the sequential image fields of view, wherein the stitching error exceeds a predefined threshold; and compensate, using a fallback model, for the stitching error of the stitching.

2. The apparatus of claim 1, wherein the at least a processor is further configured to instantiate a hybrid controller, wherein the hybrid controller selects the fallback model as a function of a coherence datum, wherein the fallback model comprises a graph-based algorithm.

3. The apparatus of claim 2, wherein the at least a processor is further configured to adjust, using a displacement continuity protocol, upstream global coordinates of previously acquired fields of view of the sequential image fields of view, wherein the previously acquired fields of view comprise a partially connected pattern.

4. The apparatus of claim 2, wherein the at least a processor is further configured to:

identify a lower connected segment that deviates from an upper segment; and adjust, using constrained least-squares optimization, a row-wise position, wherein adjusting the row-wise position comprises an upward adjustment of the lower connected segment.

5. The apparatus of claim 1, wherein the at least a processor is further configured to:

segment a slide image of the plurality of slide images into a local foreground region and an isolated background region;

stitch, using one or more local displacement equations, each local region into the global mosaic; and compensate, using the fallback model, for the stitching error in the global mosaic.

6. The apparatus of claim 5, wherein the local foreground region corresponds to a disconnected tissue island.

7. The apparatus of claim 5, wherein the at least a processor is further configured to:

generate a connectivity confidence score as a function of variance of residuals, overlap entropy, and texture score of the sequential image fields of view; and weight, using the connectivity confidence score, the one or more local displacement equations.

8. The apparatus of claim 1, wherein the at least a processor is further configured to:

identify a reference image of the sequential image fields of view, wherein identifying the reference image is a function of a stabilization protocol; and stabilize the global coordinates assigned by the positioning model.

9. The apparatus of claim 1, wherein the at least a processor is further configured to post-process, using a concurrent post-processing module, the global mosaic, wherein post-processing the global mosaic comprises generating a panorama of the global mosaic.

10. A method of real-time global positioning of images, wherein the method comprises:

acquiring, using at least a processor and an image acquisition engine operating on the at least a processor, sequential image fields of view, wherein the sequential image fields of view comprise a plurality of slide images;

determining, using the at least a processor, relative displacements between overlapping fields of view of the sequential image fields of view;

constructing, using the at least a processor, a system of linear equations representing the relative displacements;

stitching, using the at least a processor and a positioning model, the sequential image fields of view by:

estimating the system of linear equations in matrix form as a function of weighted least-squares minimization;

assigning global coordinates to each fields of view in real-time; and generating a global mosaic as a function of the global coordinates;

monitoring the stitching of the sequential image fields of view;

identifying a stitching error of the sequential image fields of view, wherein the stitching error exceeds a predefined threshold; and compensating, using a fallback model, for the stitching error of the stitching.

11. The method of claim 10, further comprising instantiating, using the at least a processor, a hybrid controller, wherein the hybrid controller selects the fallback model as a function of a coherence datum, wherein the fallback model comprises a graph-based algorithm.

12. The method of claim 11, further comprising adjusting, using a displacement continuity protocol, upstream global coordinates of previously acquired fields of view of the sequential image fields of view, wherein the previously acquired fields of view comprise a partially connected pattern.

13. The method of claim 11, further comprising:

identifying, using the at least a processor, a lower connected segment that deviates from an upper segment; and adjusting, using constrained least-squares optimization, a row-wise position, wherein adjusting comprises an upward adjustment of the lower connected segment.

14. The method of claim 10, further comprising:

segmenting, using the at least a processor, a slide image of the plurality of slide images into a local foreground region and an isolated background region;

stitching, using one or more local displacement equations, each local region into the global mosaic; and compensating, using the fallback model, for the stitching error in the global mosaic.

15. The method of claim 14, wherein the local foreground region corresponds to a disconnected tissue island.

16. The method of claim 14, further comprising:

generating, using the at least a processor, a connectivity confidence score as a function of variance of residuals, overlap entropy, and texture score of the sequential image fields of view; and weighting, using the connectivity confidence score, the one or more local displacement equations.

17. The method of claim 10, further comprising:

identifying, using the at least a processor, a reference image of the sequential image fields of view, wherein identifying the reference image is a function of a stabilization protocol; and stabilizing, using the at least a processor, the global coordinates assigned by the positioning model.

18. The method of claim 10, further comprising post-processing, using a concurrent post-processing module, the global mosaic, wherein post-processing comprises generating a panorama of the global mosaic.

19. An apparatus for real-time global positioning of images, wherein the apparatus comprises:

at least a computing device, wherein the at least a computing device comprises:

a memory; and at least a processor communicatively connected to the memory, wherein the memory contains instructions configuring the at least a processor to:

acquire, using an image acquisition engine, sequential image fields of view, wherein the sequential image fields of view comprise a plurality of slide images;

determine relative displacements between overlapping fields of view of the sequential image fields of view;

construct a system of linear equations representing the relative displacements;

stitch, using a positioning model, the sequential image fields of view by:

estimating the system of linear equations in matrix form as a function of weighted least-squares minimization;

assigning global coordinates to each field of view in real-time; and generating a global mosaic as a function of the global coordinates;

identify a reference image of the sequential image fields of view, wherein identifying the reference image is a function of a stabilization protocol; and stabilize the global coordinates assigned by the positioning model.

20. A method of real-time global positioning of images, wherein the method comprises:

acquiring, using at least a processor and an image acquisition engine operating on the at least a processor, sequential image fields of view, wherein the sequential image fields of view comprise a plurality of slide images;

determining, using the at least a processor, relative displacements between overlapping fields of view of the sequential image fields of view;

constructing, using the at least a processor, a system of linear equations representing the relative displacements;

stitching, using the at least a processor and a positioning model, the sequential image fields of view by:

estimating the system of linear equations in matrix form as a function of weighted least-squares minimization;

assigning global coordinates to each fields of view in real-time; and generating a global mosaic as a function of the global coordinates;

identifying, using the at least a processor, a reference image of the sequential image fields of view, wherein identifying the reference image is a function of a stabilization protocol; and stabilizing, using the at least a processor, the global coordinates assigned by the positioning model.

* * * * *